United States Patent
Brands et al.

(10) Patent No.: US 6,617,332 B1
(45) Date of Patent: Sep. 9, 2003

(54) TAN-1057 DERIVATIVES

(75) Inventors: Michael Brands, Wuppertal (DE); Mazen Es-Sayed, Langenfeld (DE); Dieter Häbich, Wuppertal (DE); Siegfried Raddatz, Köln (DE); Joachim Krüger, Wuppertal (DE); Rainer Endermann, Wuppertal (DE); Reinhold Gahlmann, Wuppertal (DE); Hein-Peter Kroll, Wuppertal (DE); Frank-Ulrich Geschke, Wuppertal (DE); Armin de Meijere, Göttingen (DE); Vladimir N. Belov, Göttingen (DE); Victor Sokolov, St. Petersburg (RU); Sergej Kozhushkov, Göttingen (DE); Markus Kordes, Frankenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/763,711

(22) PCT Filed: Aug. 20, 1999

(86) PCT No.: PCT/EP99/06124
§ 371 (c)(1),
(2), (4) Date: Apr. 11, 2001

(87) PCT Pub. No.: WO00/12484
PCT Pub. Date: Mar. 9, 2000

(30) Foreign Application Priority Data

Aug. 27, 1998 (DE) .......................... 198 38 998

(51) Int. Cl.$^7$ .................... C07D 239/22; A61K 31/513
(52) U.S. Cl. .................. 514/272; 544/320; 544/321
(58) Field of Search ................... 514/272; 544/320, 544/321

(56) References Cited

FOREIGN PATENT DOCUMENTS

| EP | 0339596 | 3/1994 |
|---|---|---|
| EP | 0 339 596 B1 * | 3/1994 |
| WO | 9907685 | 2/1999 |

OTHER PUBLICATIONS

Williams et al. JACS, 1997, 119, 11777–11784.*
Funabashi, Y., Tsubotani, S., Koyama, K., Katayama, N., and Harada, S., "A New Anti–MRSA Dipeptide, TAN–1057 A", Tetrahdron, 49(1): 13–28 (1993).
Katayama, N., Fukusumi, S., Funabashi, Y., Iwahi, T., and Ono, H., "Tan–1057 A~D, New Antibiotics with Potent Antibacterial Activity Against Methicillin–Resistant *Staphylococcus aureus*. Taxonomy, Fermentation and Biological Activity", Journal of Antibiotics, 46(4): 606–613 (Apr. 1993).

Sokolov, V.K., Kozhushkov, S. I., Nikolskaya, S., Belov, V. N., Es–Sayed, M., and De Meijere, A., "Total Synthesis of TAN–1057 A/B, a New Dipeptide Antibiotic from Flexibacter sp. PK–74", Eur. J. Org. Chem., pp. 777–783 (1998).

Bastiaans, H. M. M., "Alewijnse, A. E., Van Der Baan, J. L., and Ottenheijm, C. J., A Facile Conversion of Arginine into β–Homomarginine Dipeptides", Tetrahedron Letters, 35(41): 7659–7660 (1994).

Profft, V. E., and Becker, F.–J., "Uber die Kondensation von β–Aryl–β–Amino–Sauren mit δ–Valero– und εCaprolactimathern und die Cyclisierungsmoglichkeit der Erhaltenen Kondensationsprodukte", Jounral fur Praktische Chemie, Series 4, vol. 30, pp. 18–38 (1965).

Su, W., "A Convenient Synthesis of Di–(Benzyloxycarbonyl)–Protected Guanidines", Synthetic Communications, 26(2): 407–413 (1996).

Greene, T. W., and Wuts, P. G. M., *Protective Groups in Organic Synthesis*, 2$^{nd}$ ed., John Wiley & Sons, Inc., New York (1991).

Houben–Weyl, *Method of Organic Chemistry*, vol. XV/1 and 2 (1974).

Williams, R. M.; Yuan, C.; Lee, V.J., and Chamberland, S., "Synthesis and Antimicrobial Evaluation of TAN–1057A/B Analogs", J. Antibiot., 51(2): 189–201 (Feb. 1998).

Yuan, C.; and Williams, R. M., "Total Synthesis of the Anti Methicillin–Resistant *Staphylococcus aurenus* Peptide Antibiotics TAN–1057A–D", J. Am. Chem. Soc., 119: 11777–11784 (1997).

* cited by examiner

Primary Examiner—Richard L. Raymond
Assistant Examiner—H Kahsay

(57) ABSTRACT

The invention relates to novel natural product derivatives of the formula (I), to processes for their preparation, to pharmaceutical compositions comprising them and to their use in the treatment of disorders in humans or animals:

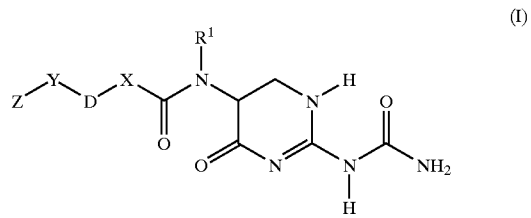

in which $R^1$, D, X, Y and Z are defined as in claim 1.

19 Claims, No Drawings

TAN-1057 DERIVATIVES

The present invention relates to novel natural product derivatives, to processes for their preparation, to pharmaceutical compositions comprising them and to their use in the treatment of disorders in humans or animals.

EP-A-0339596 discloses antibiotics of the formula

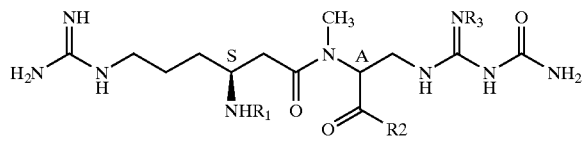

which are obtained by cultivating a microorganism of the genus Flexibacter.

Specifically, this publication also describes the following compounds

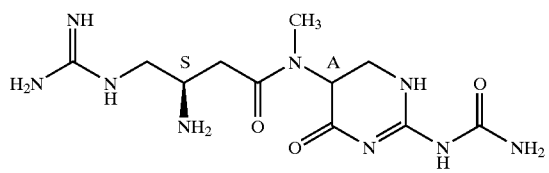

in which the carbon atom A has the S configuration (TAN-1057A) or the R configuration (TAN-1057B). Y. Funabashi et al.; Tetrahedron 49, 13, 1993 describe the chemical and structural characterization of TAN-1057A and TAN-1057. B. N. Katayama et al.; J. Antibiotics, 46, 606, 1993 report about the taxonomy of TAN-1057-producing organisms and the biological properties of TAN-1057. Total syntheses of TAN-1057 compounds were published by C. Yuan and R. M. Williams in J. Am. Chem. Soc.; 119, 11777, 1997 and A. de Meijere et al. in Eur. J. Org. Chem. 1998, 777. First derivatives of TAN-1057 compounds were described by R. M. Williams in J. Antibiotics; 51, 189, 1998. However, most of the derivatizations relate to the cyclic amidinourea moiety of the molecule. Thus, for example, derivatives of the type

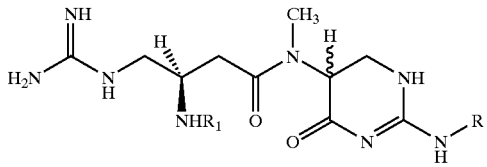

in which R represents Ac, COPh, COOMe, SO$_2$Me and CO$_2$CH$_2$Ph are described.

WO 99/07685, which was published after the date of priority of the present application, discloses derivatives, acylated at the cyclic amidinourea moiety of the molecule and additionally phosphorylated, of the general formula:

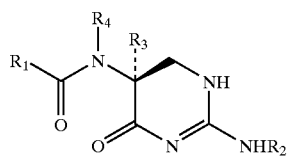

in which R$_2$ represents

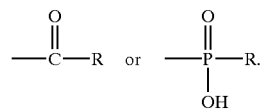

Only two derivatizations (J. Antibiotics; 51, 189, 1998) relate to the (S)-β-homoarginine moiety:

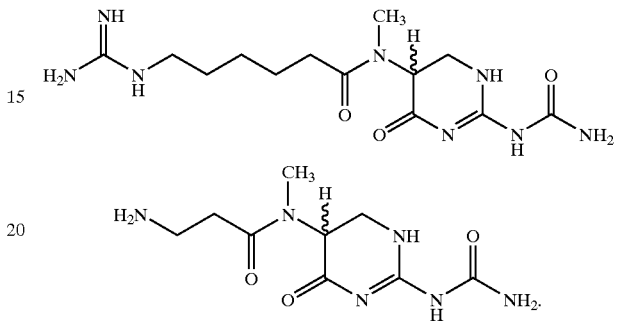

However, these derivatizations resulted in a complete loss of biological activity.

It was the object of the inventors of the present invention to synthesize further derivatives of the TAN-1057 compounds to investigate their biological and/or pharmacological actions. After overcoming difficult synthetic problems, the inventors succeeded in synthesizing further novel compounds which are derivatized in the (S)-β-homoarginine moiety of TAN 1057, using a novel, generally applicable process, which compounds, surprisingly, have considerably lower toxicity, with comparable activity.

Accordingly, the present invention provides compounds of the general formula:

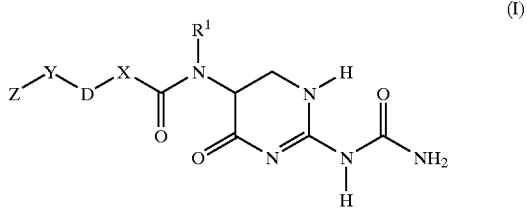

in which

R$^1$ represents hydrogen or (C$_1$–C$_6$)alkyl,

X represents a group of the formula —(CH$_2$)$_m$—, in which m is 0, 1 or 2,

D is selected from groups of the formulae D$_1$ to D$_3$

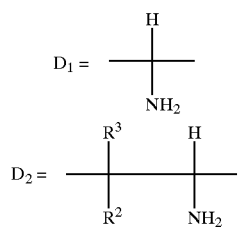

-continued

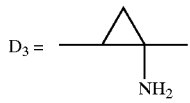

in which $R^2$ represents hydrogen or hydroxyl,
$R^3$ represents hydrogen, or
$R^2$ and $R^3$ together form an oxo group,
Y represents a straight-chain or branched $(C_1-C_5)$ alkanediyl group in which optionally one carbon atom may be replaced by —O— or —NH— and which may optionally be substituted by hydroxyl or oxo, or represents a group of the formulae below

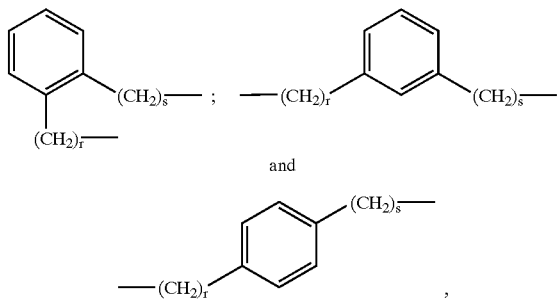

in which r and s are identical or different and are 0, 1 or 2,
Z represents a group selected from groups of the formulae

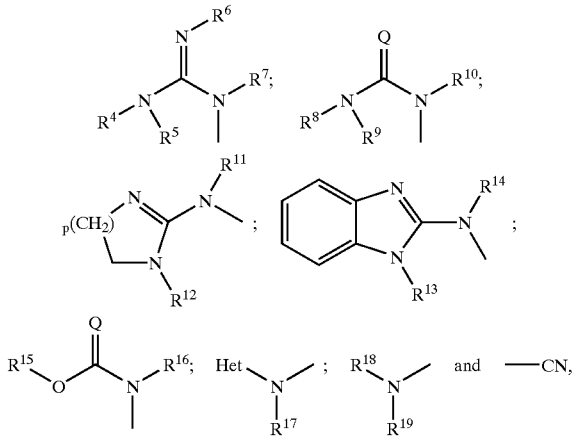

in which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ in each case independently of one another are selected from the group consisting of hydrogen, $(C_1-C_6)$alkyl, $(C_1-C_4)$ alkanoyl, t-butoxycarbonyl, benzyloxycarbonyl and benzyl,
Q represents oxygen or sulphur and
p is 1, 2 or 3 and
Het represents a 5- or 6-membered heteroaromatic group having 1 to 4 nitrogen atoms,
except for compounds in which
$R^1$ represents methyl, m is 1, D represents $D_1$, Y represents —$(CH_2)_3$— and Z represents a group of the formula

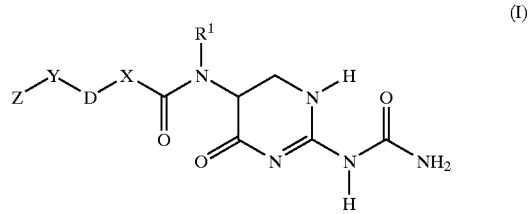

and pharmaceutically acceptable salts thereof.

The case corresponding to TAN 1057A/B, in which $R^1$ represents methyl, m is 1, D represents $D_1$, Y represents —$(CH_2)_3$— and Z represents a group of the formula

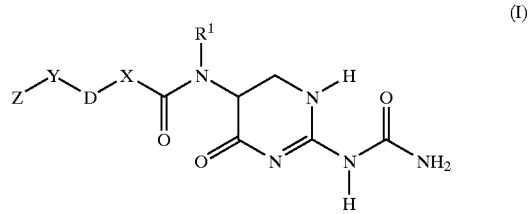

which is excluded from the compounds claimed according to the invention, corresponds to the case in which D represents $D_2$, $R^2$ and $R^3$ represent hydrogen, R represents methyl, m is 1, Y represents —$(CH_2)_2$— and Z represents a group of the formula

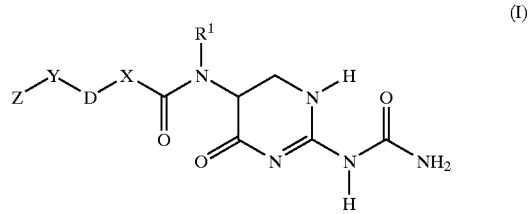

which, as a consequence, is likewise excluded from the compounds according to the invention.

The present invention preferably provides compounds of the general formula:

(I)

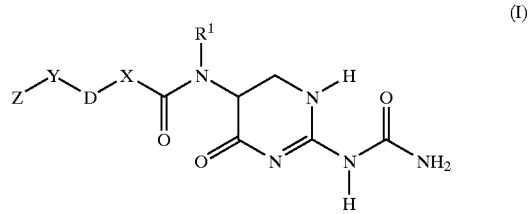

in which $R^1$ represents hydrogen or $(C_1-C_6)$alkyl,

X represents a group of the formula —$(CH_2)_m$—, in which m is 0, 1 or 2,

D is selected from groups of the formulae $D_1$ to $D_3$

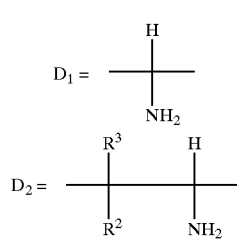

-continued

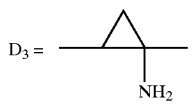

in which R² represents hydrogen or hydroxyl,
R³ represents hydrogen, or
R² and R³ together form an oxo group,
Y represents a straight-chain or branched (C₁–C₅) alkanediyl group in which optionally one carbon atom may be replaced by —O— or —NH— and which may optionally be substituted by hydroxyl or oxo, or represents a group of the formulae below

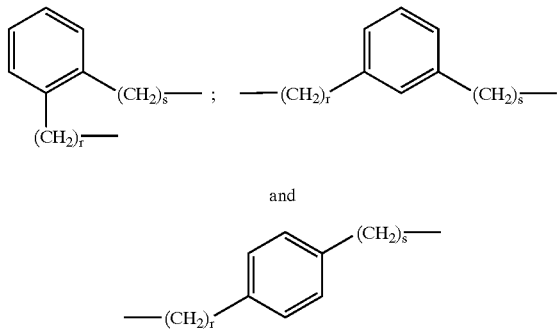

and in which r and s are identical or different and are 0, 1 or 2,
Z represents a group selected from groups of the formulae

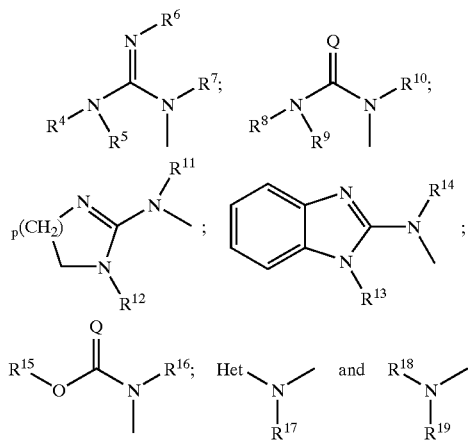

in which R⁴, R⁵, R⁶, R⁷, R⁸, R⁹, R¹⁰, R¹¹, R¹², R¹³, R¹⁴, R¹⁵, R¹⁶, R¹⁷, R¹⁸ and R¹⁹ in each case independently of one another are selected from the group consisting of hydrogen, (C₁–C₆)alkyl, (C₁–C₄)alkanoyl, t-butoxycarbonyl, benzyloxycarbonyl and benzyl,
Q represents oxygen or sulphur and
p is 1, 2 or 3 and
Het represents a 5- or 6-membered heteroaromatic group having 1 to 4 nitrogen atoms,
except for compounds in which R¹ represents methyl, m is 1, D represents D₁, Y represents —(CH₂)₃— and Z represents a group of the formula

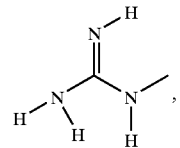

(corresponds to the case in which D represents D₂, R² and R³ represent hydrogen, R¹ represents methyl, m is 1, Y represents —(CH₂)₂— and Z represents a group of the formula

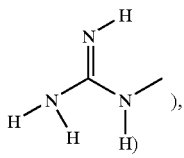

and pharmaceutically acceptable salts thereof.

m in the group of the formula —(CH₂)ₘ— for X is preferably 1 or 2. Accordingly, the group of the formula —(CH₂)ₘ— for X preferably includes a methylene or an ethylene (ethane-1,2-diyl) group. X is particularly preferably a methylene group.

A straight-chain or branched (C₁–C₅)alkanediyl group in which optionally one carbon atom may be replaced by —O— or —NH— and which, additionally, may optionally be substituted by hydroxyl or oxo, in the definition of Y includes, for example, straight-chain (C₁–C₅)alkanediyl groups, such as methylene, ethylene, propane-1,3-diyl, butane-1,4-diyl and pentane-1,5-diyl. Preference is given to straight-chain (C₁–C₄)alkanediyl groups.

A straight-chain or branched (C₁–C₅)alkanediyl group in which one carbon atom is replaced by —O— or —NH— and which, additionally, may optionally be substituted by hydroxyl or oxo, in the definition of Y includes, for example, groups of the formulae:

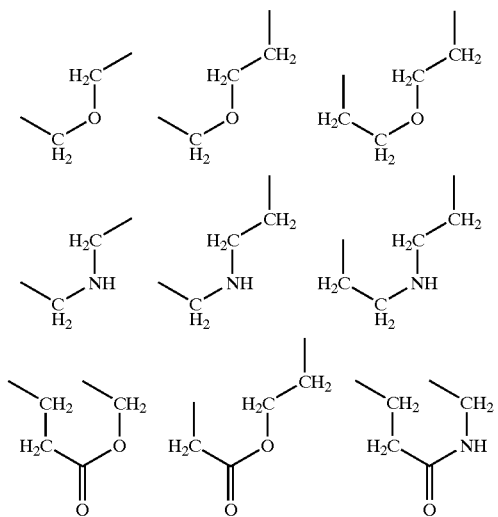

-continued

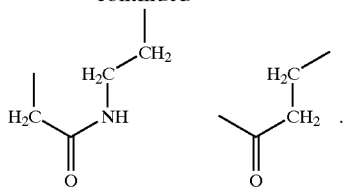

Here, either side of the groups may be attached to Z. The groups of the formulae

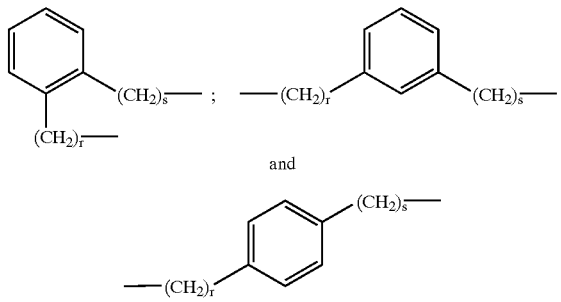

for Y include, for example, symmetrical radicals in which r and s are identical, or asymmetrical radicals; symmetrical radicals in which r and s are 0, i.e. 1,2-phenylene, 1,3-phenylene and 1,4-phenylene, being preferred. Particular preference is given to 1,3- or m-phenylene.

In the general formula (I), Z is selected from groups of the formulae

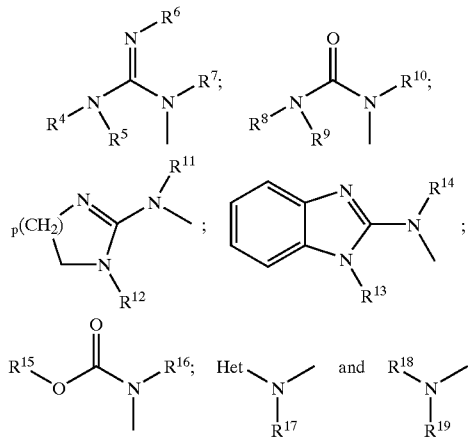

in which $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ in each case independently of one another are selected from the group consisting of hydrogen, $(C_1-C_6)$alkyl, $(C_1-C_4)$alkanoyl, t-butoxycarbonyl, benzyloxycarbonyl and benzyl, Q represents oxygen or sulphur and p is 1, 2, or 3 and Het represents a 5- or 6-membered heteroaromatic group having 1 to 4 nitrogen atoms.

Among these groups for Z

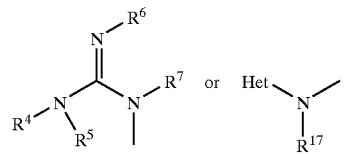

$R^4$, $R^5$, $R^6$, $R^7$ and $R^{17}$ are as defined above are preferred.

Z is particularly preferably a group of the formula

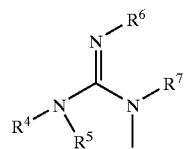

in which $R^4$, $R^5$, $R^6$ and $R^7$ are as defined above, preferably hydrogen.

In the group of the formula

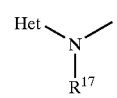

for Z, Het is advantageously selected from the group consisting of the group of the formulae:

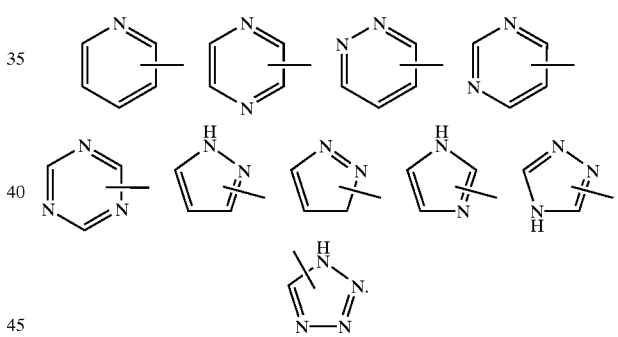

Here, the azoles, i.e. the five-membered unsaturated heterocyclic ring systems having 1 to 4 nitrogen atoms, can be attached either via a carbon or via a nitrogen atom.

Among these radicals, six-membered heteroaromatics having 1 to 3 nitrogen atoms are preferred.

Particularly preferably, Het represents pyridyl, including 2-pyridyl, 3-pyridyl and 4-pyridyl, 2-pyridyl being particularly preferred.

Very particularly preferably, Z represents

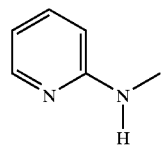

In a further preferred embodiment, Z represents a group of the formula

in which $R_{18}$ and $R^{19}$ are as defined above.

$(C_1-C_6)$Alkyl in the above definitions of $R^1$ and $R^4$ to $R^{19}$ represents a straight-chain or branched alkyl group having 1 to 6 carbon atoms such as, for example, methyl, ethyl, n-propyl, iso-propyl, n-butyl, tert-butyl, sec-butyl, iso-butyl, pentyl and hexyl, preference being given to $(C_1-C_4)$alkyl groups and particular preference being given to methyl.

$R^4$ to $R^{19}$ preferably represent hydrogen.

$(C_1-C_4)$Alkanoyl in the definition of $R^4$ to $R^{19}$ represents, for example, formyl, acetyl, propionyl and butanoyl, preference being given to formyl and acetyl.

Q preferably represents oxygen.

p is preferably 1 or 2.

In a preferred embodiment of the invention, the group D represents

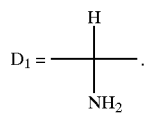

In a further preferred embodiment of the invention, the group D represents

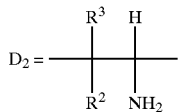

in which $R^2$ and $R^3$ are as defined above and are preferably hydrogen.

In a preferred embodiment of the invention, the group D represents

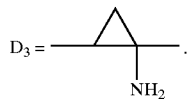

Among these, preference is given to the groups $D_1$ and $D_2$ and particular preference is given to $D_1$. Preference is furthermore given to the case in which both $R^1$ and $R^2$ in $D_2$ are hydrogen.

Suitable pharmaceutically acceptable salts of the compounds of the general formula (I) can be conventional non-toxic salts including, for example, salts with mineral acids, carboxylic acids or sulphonic acids. Such acid addition salts include organic acid salts (for example acetates, propionates, lactates, citrates, benzoates, trifluoroacetates, maleates, tartrates, fumarates, methanesulphonates, ethanesulphonates, benzenesulphonates, formates, toluenesulphonates, naphthalene-disulphonates, etc.) and inorganic acid salts (for example hydrochlorides, hydrobromides, hydrolodides, sulphates, nitrates, phosphates, etc.).

As a consequence of double bonds and asymmetric carbon atoms, the compounds of the general formula (I) can be present as stereoisomers, such as cis/trans isomers and configuration isomers, such as enantiomers or diastereomers; these isomers and mixtures thereof are included in the scope of the present invention.

The compounds according to the invention are prepared by reacting compounds of the formula (II)

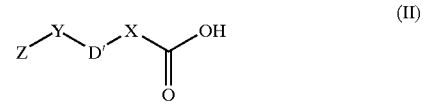

in which X, Y and Z are as defined above and D' is selected from groups of the formulae $D'_1$ to $D'_3$

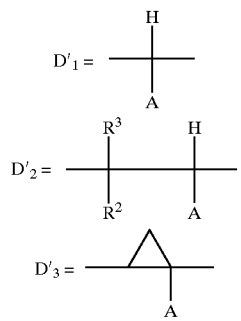

in which $R^2$ and $R^3$ are as defined above and A is a conventionally protected amino group, with compounds of the formula (III)

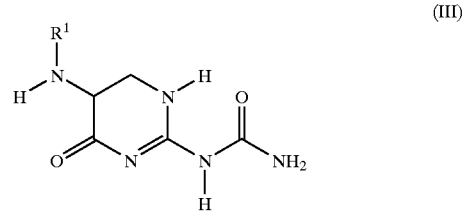

in which $R^1$ is as defined above, in the presence of coupling agents, if desired in the presence of bases, and the conventional protective group in the protected amino group A is removed by methods known per se.

The compound of the formula (III) is synthesized using the method of V. V. Sokolov, S. I. Kozhushkov, S. Nikolskaya, V. N. Belov, M. Es-Sayed, A. de Meijere, *Eur. J. Org. Chem.* 1998, 777.

Compounds of the formula (II) used for the amide formation are appropriately protected amino acids which can be obtained, for example, by chain extension from the α-amino acids (cf. H. M. M. Bastiaans, A. E. Alewijnse, J. L. van der Baan, H. C. J. Ottenheijm, *Tetrahedron Lett.* 1994, 35, 7659).

If the straight-chain or branched $(C_1-C_5)$alkanediyl group for Y contains functional groups, such as hydroxyl, keto, ester or amide functions, their introduction or synthesis is carried out by standard methods (see, for example, Houben-Weyl, Methoden der organischen Chemie [Methods of organic chemistry], Volume XV/1 and 2.).

3-(Benzyloxycarbonylamino)-3-[3'-(N-benzyloxycarbonylguanidino)phenyl]-propionic acid, for example, is prepared according to Scheme 1 below.

Scheme 1

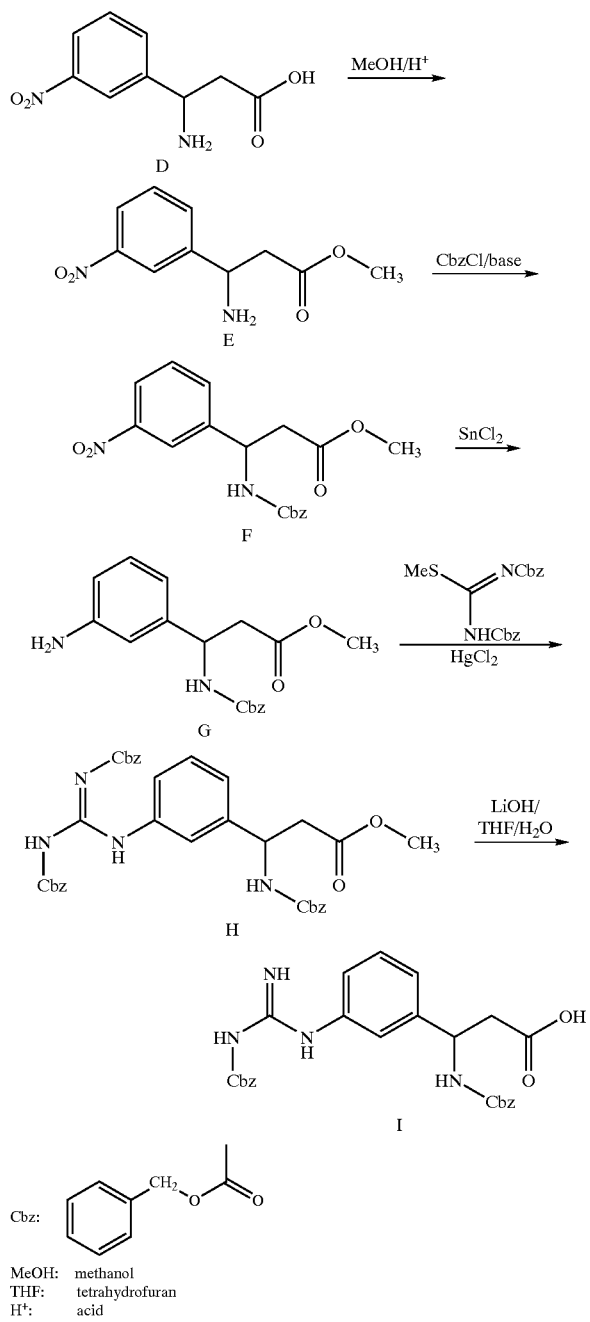

MeOH: methanol
THF: tetrahydrofuran
H⁺: acid

Here, compound D (E. Proft, F.-J. Becker, *J. prakt Chemie* 1965, 30, 18), for example, is esterified with methanol in the presence of, for example, concentrated sulphuric acid. In the two-phase system dichloromethane/base, such as, for example, saturated aqueous sodium bicarbonate solution, the free amino group is converted into the benzyl carbamate using benzyl chloroformate. The aromatic nitro group is reduced using tin(II) chloride. Subsequent reaction with bis(benzyloxycarbonyl) S-methylthiourea (W. Su, Synth. Commun. 1996, 26, 407) in the presence of mercury(II) chloride and basic hydrolysis of the methyl ester gives the carboxylic acid I.

In the above reactions, it is also possible to use the generally employable solvents, acids and bases listed below in place of those mentioned here.

The compounds of the formula (II) in which D represents $D_3$ are prepared, for example, as illustrated in the following example:

Scheme 2

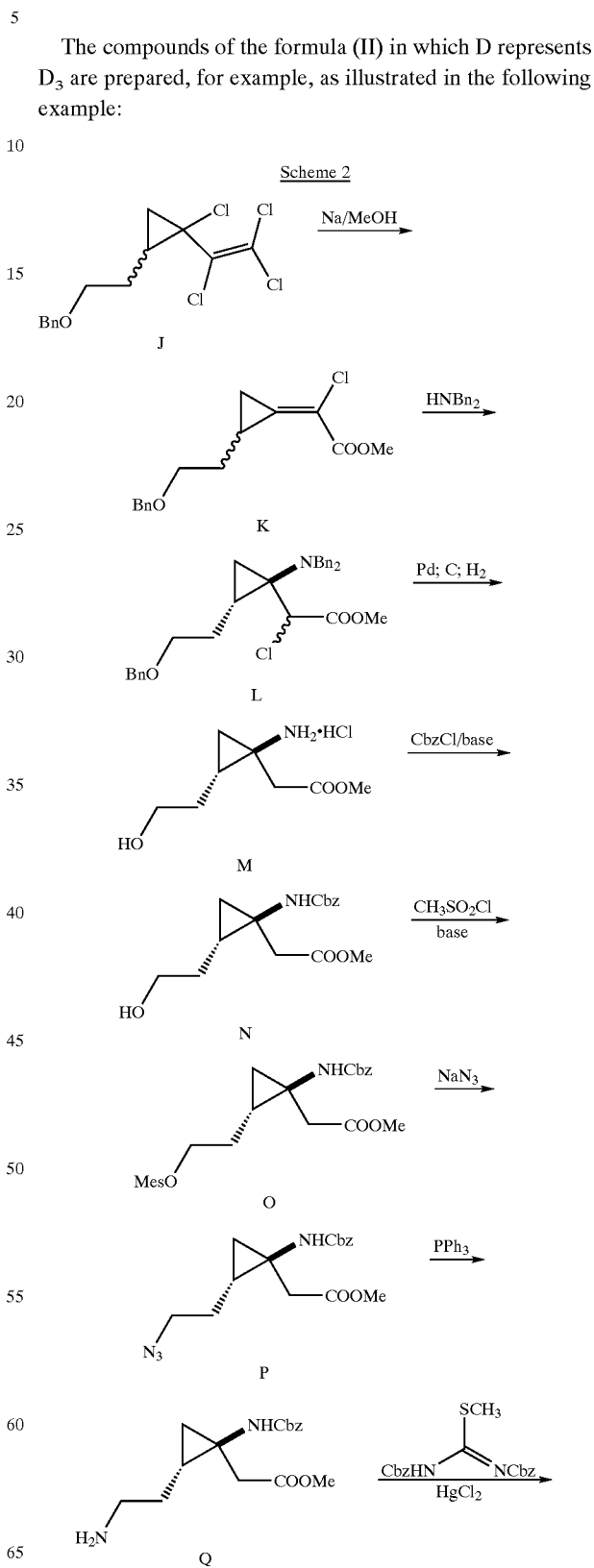

-continued

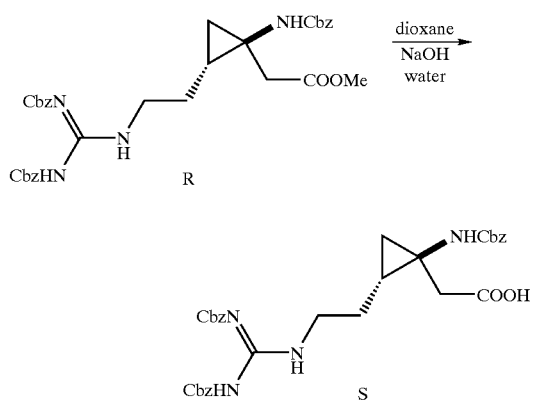

Here:

Bn represents: —CH$_2$—Ph
Cbz represents: PhCH$_2$—O—C(O)—
Mes represents: CH$_3$S$_{N2}$—
Me represents: methyl The reactions are preferably carried out under the conditions described in the experimental section.

The radical Z in the acid component of the formula (II) is, in principle, synthesized by reacting an S-methyl thiourea derivative with a terminal amino group. This reaction is mediated by basic reagents, such as tertiary amines or sodium hydroxide, if appropriate in the presence of mercury (II) chloride.

If Z is a carbamate group, the carbamate group is obtained by reacting the terminal amino group with a chloroformic ester in the presence of a base (for example a tertiary amine or sodium hydroxide) (Scheme 3). Here, the acid function can be present in free form or blocked by an appropriate protective group (for example an alkyl ester).

Scheme 3

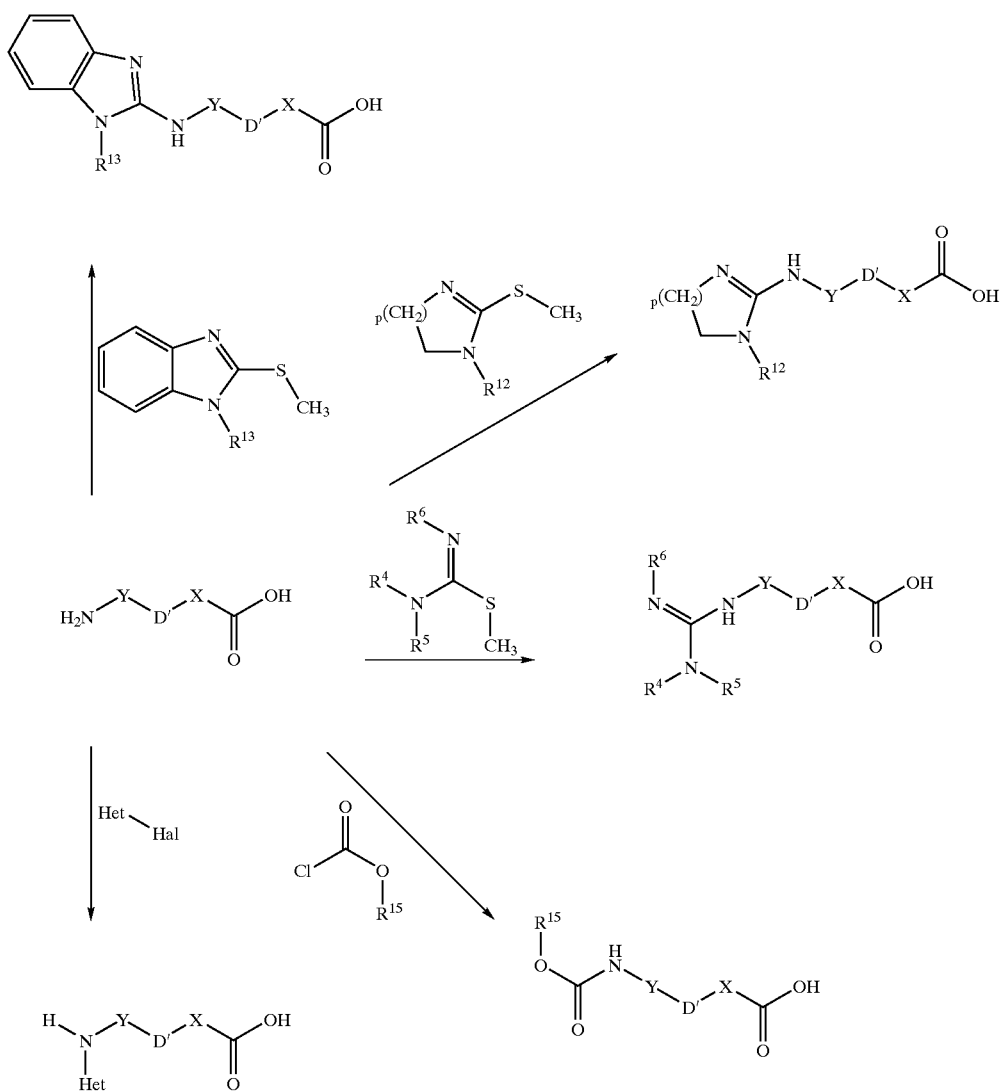

Here, the substituents or substituent groups are as defined above, and Hal represents halogen, such as fluorine, chlorine, bromine and iodine.

In the case that $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ in the above process are not hydrogen but $(C_1-C_6)$alkyl, $(C_1-C_4)$alkanoyl, t-butoxycarbonyl, benzyloxycarbonyl and benzyl, the amino groups are alkylated by customary methods, for example using alkylating agents, such as alkyl halides, sulphonic esters or substituted or unsubstituted dialkyl- or diarylsulphonates, such as methyl iodide or dimethyl sulphate, and $(C_1-C_4)$alkanoyl, t-butoxycarbonyl, benzyloxycarbonyl and benzyl, which are conventional amino protective groups, are introduced by customary methods (cf. T. W. Greene, P. G. M. Wuts, Protective Groups in Organic Synthesis, 2nd edition, John Wiley and Sons, New York, 1991).

The conventional amino protective group in the conventionally protected amino group A is advantageously removed using the methods described below.

Suitable for use as coupling agents in the reaction of the compounds of the formula (II) and (III) are known reagents, such as, for example, O-(7-azabenzotriazol-1-yl)-1,1,3,3-tetramethyluronium hexafluorophosphate (HATU) or bromo-tris-pyrrolidino-phosphonium hexa-fluorophosphate (PyBroP), since their use ensures a smooth coupling with high yields.

Suitable for use as conventional amino protective groups in the conventionally protected amino group A (i.e. the conventionally protected —$NH_2$ group) are customary amino protective groups used in peptide chemistry. These preferably include: benzyloxycarbonyl, 2,4-dimethoxybenzyloxycarbonyl, 4-methoxy-benzyloxycarbonyl, methoxycarbonyl, ethoxycarbonyl, tert.-butoxycarbonyl, allyl-oxycarbonyl, phthaloyl, 2,2,2-trichloroethoxycarbonyl, fluorenyl-9-methoxycarbonyl, formyl, acetyl, 2-chloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl, 4-methoxyphenyl or triphenylmethyl, particular preference being given to benzyloxycarbonyl.

The removal of the amino protective group in the conventionally protected amino group A is carried out by conventional methods (cf. T. W. Greene, P. G. M. Wuts, Protective Groups in Organic Synthesis, 2nd edition, John Wiley and Sons, New York, 1991), namely, preferably, tert-butyloxycarbonyl using hydrochloric acid in dioxane, fluorenyl-9-methoxycarbonyl using piperidine and benzyloxycarbonyl by hydrogenolysis in the presence of catalysts such as, for example, with Rancy nickel, palladium, palladium on carbon or platinum or preferably palladium(II) chloride. Any amino protective groups present in group Z, such as, for example, benzyloxycarbonyl, can also be removed in this reaction.

In the present invention, the reactions are carried out in inert organic solvents which do not change under the reaction conditions. These include ethers, such as diethyl ether, 1,4-dioxane or tetrahydrofuran, halogenated hydrocarbons, such as dichloromethane, trichloromethane, carbon tetrachloride, 1,2-dichloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents. Particular preference is given to dichloromethane, tetrahydrofuran, dioxane, methanol or dimethylformamide.

The reactions are generally carried out in a temperature range of from 0° C. to 150° C., preferably from 0° C. to 70° C. The reactions can be carried out under atmospheric, elevated or under reduced pressure (for example from 0.5 to 5 bar). In general, they are carried out under atmospheric pressure.

Suitable bases for the processes according to the invention are, in general, sodium bistrimethylsilylamide or lithium bistrimethylsilylamide, alkali metal hydroxides, such as sodium hydroxide, lithium hydroxide or potassium hydroxide, sodium bicarbonate, sodium hydride or organic (trialkyl($C_1-C_6$)amines) such as triethylamine, or heterocycles, such as 1,4-diazabicyclo[5.4.0]undec-7-ene (DBU), pyridine, diaminopyridine, methylpiperidine or N-methylmorpholine. Preference is given to lithium hydroxide, sodium bicarbonate, pyridine, diisopropylethylamine and triethylamine.

A suitable acid can include an organic acid (for example formic acid, acetic acid, propionic acid, trichloroacetic acid, trifluoroacetic acid, etc.), an inorganic acid (for example hydrochloric acid, hydrobromic acid, sulphuric acid, hydrogen chloride, hydrogen bromide, hydrogen fluoride, etc.) etc.

The natural product derivatives of the present invention have interesting pharmacological actions. In particular, the compounds of the present invention have antibacterial action, and they are therefore effective in the control of bacterial infections in humans and animals. Furthermore, the known compounds TAN-1057 A and B have the problem that the treated germs rapidly become resistant to these compounds, and it is thought that the compounds of the present invention may less rapidly lead to the development of resistance, whilst having comparable antibacterial activity.

TAN1057 A,B shows pronounced toxicity in the liver and cells of the immune system, which virtually excludes a use of this substance for the therapy of bacterial infections. Compared to TAN 1057 A,B, all compounds of the invention have reduced toxicity, which may permit therapeutical use.

Determination of the Minimum Inhibitory Concentration (MIC)

The MIC was determined using the liquid dilution test. Overnight cultures of the test germs (*S. aureus* 133) in Isosensitest bouillon were diluted 1:1000 with foetal calf serum (FCS) or Isosensitest bouillon and incubated with dilutions of the test substances (successive dilutions of 1:2).

Selection of TAN 1057 A,B-resistant Bacteria

Bacteria of the strain *S. aureus* 133 were incubated with different concentrations of TAN 1057 A,B for 24 hours. Bacteria which showed visible growth at elevated TAN 1057 A,B concentrations were transferred into new culture bottles with different TAN 1057 A,B concentrations and incubated again. This process was repeated for several days, selecting step by step bacteria having increased resistance to TAN 1057 A,B. The MIC of highly resistant *S. aureus* 133 bacteria was >100 µg/ml (initial MIC: <0.1 µg/ml). The bacteria from this selection series, having an MIC of <0.1, 0.8, 25, 100 and >100 µg/ml, were used for tests. It is thus possible to identify TAN 1057 A,B derivatives having antibacterial activity against TAN 1057 A,B-resistant cells.

Toxicological Studies

Description of the Methods

Compatibility tests of the exemplary compounds were carried out using cultures of eukaryotic cells. Hepatocytes (HepG2) and murine macrophage cells (J774.A1) were used as indicator for organ-specific toxicity. The murine macrophage cell line used is a particularly sensitive indicator for toxic effects. All derivatives tested showed lower toxicity than TAN 1057 A,B.

Test with HepG2 Cells:

The vitality and functionality of human HepG2 liver cells were examined after treatment with exemplary compounds. In each case $2 \times 10^4$–$1 \times 10^5$ cells were incubated in RPMI 1640 (Whittacker) with 10% heat-inactivated foetal calf serum (Gibco) at 37° C. for 40–48 hours. The incubation volume of 200 µl contained the test substances in concentrations of 10, 2 and 0.4 µg/ml.

The vitality was examined after addition of 20 µl Alamar Blue (Biosource, Art. No. DAL 1100) by measuring the fluorescence (excitation: 544 nm, emission: 590 nm).

The functionality of the HepG2 cells was examined by measuring the secretion of apo B100 and α2-macroglobulin after treatment. To this end, the protein content of the culture supernatants was determined by ELISA after incubation for 40–48 hours. Apo B100 was bound using rabbit ahLDL (1 mg/ml) and quantified using peroxidase-conjugated monoclonal antibodies (ahLDL_POD), with addition of the substrate $TMB/H_2O_2$. The optical density was measured at 450 nm.

To determine α2-macroglobulin, the ELISA system from Biodesign (Art.No. H 45205M) was used. Quantification was likewise carried out using the substrate $TMB/H_2O_2$, and measuring the optical density at 450 nm.

Test With J774.A1 Cells:

In each case $1.2 \times 10^4$ cells were incubated at 37° C. for 24 hours. Test substances were added at different concentrations, and the cells were incubated for another 72 hours. The cells were then treated with 50 µl of Neutral Red solution (Sigma, No. N 2889) for 2 hours, washed with PBS medium and denaturated using an ethanol/glacial acetic acid mixture.

The cultures were measured in an Elisa reader at 540 nm and 630 nm. The $IC_{50}$ values were extrapolated and indicate at which concentration the vitality of the cells, measured by the uptake of Neutral Red, is reduced to 50%, compared to untreated control cells.

Results

The cultures were incubated at 37° C. for 18–24 hours. In each case the lowest concentration of substance at which no visible bacterial growth took place, was defined as MIC.

| Example | MIC in FCS (S.aureus; µg/ml) |
|---|---|
| 1 | 0.2 |
| 2 | 50 |
| 3 | 100 |
| 4 | 0.4 |
| 5 | 0.1 |
| 6 | 0.8 |
| 7 | 0.8 |
| 8 | 1.6 |
| 9 | 1.6 |
| 10 | 3.2 |
| 11 | 3.2 |
| 12 | 6.3 |
| 13 | 12.5 |
| 14 | 12.5 |
| 15 | 100 |
| 16 | 100 |
| 17 | 6.3 |
| 18 | 12.5 |
| Comparative Example | |
| TAN 1057 A, B (1:1 mixture of the two epimers) | 0.1 |

The S. aureus 133 isolates with medium and high resistance to TAN 1057 A,B were tested in comparison to the derivatives of the invention. In the MIC test with the isolated which showed medium resistance to TAN 1057 A,B (MIC to TAN 1057 A,B=0.8 µg/ml), Ex. 4 showed better antibacterial activity (MIC to Example 4=0.2 µg/ml).

Test of Antibacterial Activity in vivo

Mice were infected with $1 \times 10^6$ bacteria of the strain S. aureus 133 in 5% mucine (i.p.) and treated by intravenous administration of the test substances 30 minutes after the infection. Without treatment, all infected animals died. The therapeutic doses for TAN 1057 A,B and the compound of Example 4 at which all infected animals survived (=$ED_{100}$) was 1 mg/kg for both substances.

Up to the highest test concentration, the compounds of Examples 1 and 2 show no inhibition in the vitality and functionality tests ($IC_{50} > 10$ µg/ml). In the α2-macroglobulin assay, an inhibition ($IC_{50}$ 7 µg/ml) was found for TAN 1057 A,B.

In the Neutral Red vitality test using J774.A1 cells, an $IC_{50}$ value of 0.25 µg/ml was determined for TAN 1057 A,B. All derivatives of TAN 1057 of the present invention tested show higher $IC_{50}$ values, indicating the in some cases considerably better compatibility of the compounds.

$IC_{50}$ values are listed in the table below:

| Example | $IC_{50}$ value |
|---|---|
| TAN 1057 A,B (1:1 mixture of the two epimers) | 0.25 |
| 1 | 3 |
| 2 | 6 |
| 3 | 40 |
| 4 | 25 |
| 5 | 6 |
| 6 | 5.5 |
| 7 | 50 |
| 8 | 1.8 |

Acute Toxicity of TAN 1057 A,B and the Compound of Example 4

The acute toxicity of the substances was determined by determining the dose at which 50% of the treated mice survive (=$LD_{50}$). Following intraperitoneal administration of the test substances, the LD50 for TAN 1057 A,B was 100 mg/kg. The LD50 for the compound of Example 4 was >400 mg/kg.

This result reflects the considerably lower toxicity of the compounds according to the invention. However, as described above, the therapeutic activity in vivo of TAN 1057 A,B and the compound of Example 4 was comparable.

The compounds of the general formulae (I) according to the invention have a broad antibacterial spectrum, specifically against gram-positive germs and some gram-negative bacteria, and also against corynebacteria. Owing to these properties, they can be used as chemotherapeutically active compounds in human and veterinary medicine.

With their aid, it is possible to control gram-positive germs (with particularly good action against staphylococci, including methillicin-resistant Staph. Aureus), gram-negative bacteria (for example *Moraxella catarrahlis*) and also corynebacteria and to prevent, improve and/or heal disorders caused by these pathogens.

They are highly suitable for the prophylaxis and chemotherapy of local and systemic infections caused by such pathogens, in human and veterinary medicine.

The present invention includes pharmaceutical preparations which, in addition to non-toxic inert pharmaceutically suitable carriers or excipients, comprise one or more compounds according to the invention, or which consist of one or more active compounds according to the invention, and also processes for preparing these preparations.

The active compound(s) can, if appropriate, also be present in microencapsulated form, in one or more of the abovementioned carriers.

In the abovementioned pharmaceutical preparations, the therapeutically active compounds should preferably be present in a concentration of about 0.1 to 99.5, preferably about 0.5 to 95, % by weight of the total mixture.

The abovementioned pharmaceutical preparations may, in addition to the compounds according to the invention, also comprise other pharmaceutically active compounds.

In general, it has been found to be advantageous, both in human and in veterinary medicine, to administer the active compound(s) according to the invention in total amounts of from about 0.5 to about 500, preferably 5 to 100, mg/kg of body weight per 24 hours, if appropriate in the form of a plurality of individual administrations, to obtain the desired results. An individual administration preferably contains the active compound(s) according to the invention in amounts of from about 1 to about 80, in particular 3 to 30, mg/kg of body weight.

To widen the activity spectrum and to achieve an increase in activity, it is also possible to combine the compounds according to the invention with other antibiotics.

EXAMPLES

Abbreviations:

DMF N,N-dimethylformamide

HATU O-(7-azabenzotriazol-1-yl)-1,1,3,3-tetramethyluronium hexafluorophosphate

PE petroleum ether (special benzine, b.p. 40–80° C.)

THF tetrahydrofuran

Example 1

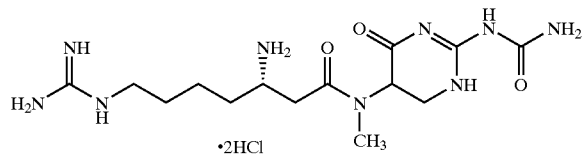

(3'S,5R,S)-5-[N-Methyl-N-(3'-amino-7'-guanidinoheptanoyl)amino]-5,6-dihydro-2-ureido-4(1H)-pyrimidone Dihydrochloride A solution of 40 mg (0.216 mmol) of (5R,S)-3,4,5,6-tetrahydro-5-methylamino-2-ureidopyrimidin-4-one, 131 mg (0.261 mmol) of (3S)-3-benzyloxycarbonylamino-7-[bis-(N-benzyloxycarbonyl)guanidino]heptanoic acid, 80 mg (0.432 mmol) of O-(7-azabenzotriazol-1-yl)-1,1,3,3-tetramethyluronium hexafluorophosphate (HATU) and 53 mg (0.432 mmol) of diisopropylethylamine in 5 ml of DMF is stirred at 23° C. for 16 h. The solvent is then removed under reduced pressure. The residue is stirred with 2 M hydrochloric acid. The aqueous phase is decanted off from the residue. The residue is taken up in dichloromethane. The organic phase is extracted twice with 2 M hydrochloric acid, dried with sodium sulphate and concentrated under reduced pressure. This gives 155 mg (93%) of the coupling product as a white solid [MS (ESI): 772 (M+H)$^+$]. The solid is dissolved in 30 ml of methanol. The solution is admixed with 65 mg (0.369 mmol) of palladium(II) chloride and stirred under an atmosphere of hydrogen (atmospheric pressure) for 4 h. The solution is filtered off and concentrated under reduced pressure. The resulting residue is stirred with diethyl ether and filtered off. This gives the title compound as a beige solid (80 mg, 93%). $^1$H-NMR (400 MHz, CD$_3$OD): 1.54 (m, 2H), 1.66 (m, 2H), 1.75 (m, 2H), 2.76 (dd, 1H), 2.98 (td, 1H), 3.17+3.36 (s, 3H), 3.21 (dd, 2H), 3.59 (m, 1H), 3.89 (m, 1H), 4.03 (m, 1H), 5.16 (m, 1H). MS (ESI) 370 (M+H)$^+$.

Example 2

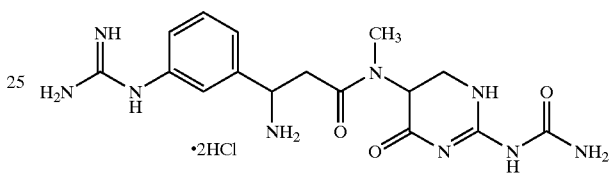

(3'RS,5RS)-5-{N-Methyl-N-[3'-amino-3'-(3-guanidylphenyl)propionyl]amino}-5,6-dihydro-2-ureido-4(1H)-pyrimidone Dihydrochloride (Compounds D to I Refer to Scheme 1)

A solution of 79.5 g (0.378 mol) D, 3-amino-3-(3-nitrophenyl)propionic acid, in 2l of methanol is admixed with 200 ml of sulphuric acid (conc.). The solution is heated at boiling point for 1 h. Most of the methanol is removed under reduced pressure and the residue is poured into ice-water. Using sodium carbonate, the pH is adjusted to 8. The aqueous phase is extracted with dichloromethane. Drying of the organic phase and removal of the solvent under reduced pressure gives the ester E, methyl 3-amino-3-(3-nitrophenyl)propionate, (52.8 g, 62%) as a white solid. 10 g (44.6 mmol) of E are dissolved in 20 ml of DMF. The solution is admixed with 12.3 g (88.2 mmol) of potassium carbonate, and 15.2 g (88.2 mmol) of benzyl chloroformate are added dropwise. The mixture is stirred at 23° C. for 2 h. The mixture is diluted with 200 ml of toluene and washed three times with water, and the organic phase is dried using sodium sulphate and concentrated under reduced pressure to give the colourless oil of methyl 3-benzyloxycarbonylamino-3-(3-nitrophenyl)propionate (12.6 g, 79%). MS (DCI/NH$_3$): 376 (M+NH$_4$)$^+$.

At 23° C., a solution of 4 g (11.1 mmol) of compound F, methyl 3-benzyloxycarbonylamino-3-(3-nitrophenyl)propionate in 20 ml of ethanol is added dropwise to a solution of 12.6 g (55.8 mmol) of tin(II) chloride dihydrate. The mixture is stirred at a bath temperature of 80° C. for 30 minutes, and most of the ethanol is then removed under reduced pressure. The residue is partitioned between water and ethyl acetae. The pH of the aqueous phase is adjusted to 8 by adding sodium bicarbonate. The mixture is filtered through a 5-cm-layer of Celite, which is washed with ethyl acetate. The phases are separated and the aqueous phase is then extracted three times with ethyl acetate. The organic phase is dried (sodium sulphate). Removal of the solvent under reduced pressure gives 3.8 g of a colourless oil G, methyl 3-benzyloxycarbonylamino-3-(3-aminophenyl) propionate, which still contains tin salts. $^1$H-NMR (200 MHz, CDCl$_3$): 2.87 (dd, 2H), 3.61 (s, 3H), 5.08 (m, 1H), 5.11 (s, 2H), 6.60 (m, 3 H), 7.11 (t, 1H), 7.35 (m, 5 H). MS (DCI/NH$_3$): 346 (M+NH$_4$)$^+$.

A solution of 0.92 g (2.8 mmol) of G, methyl 3-benzyloxycarbonylamino-3-(3-aminophenyl)-propionate and 1.0 g (2.8 mmol) of bis(benzyloxycarbonyl) S-methyl thiourea in 10 ml of DMF is admixed with 1.56 ml (11.2 mmol) of triethylamine and 0.83 g (3.1 mmol) of mercury (II)chloride. The mixture is stirred at 23° C. for 1 h, diluted with 100 ml of ethyl acetate and filtered through a 5-cm-layer of Celite. The organic phase is washed with saturated aqueous sodium bicarbonate solution and dried (sodium sulphate) and the volatile components are removed under reduced pressure. The residue is chromatographed over silica gel (dichloromethane:ethyl acetate=1:1). This gives 1.5 g (84%) of H, methyl 3-benzyloxycarbonyl-amino-3-[3-(N,N'-bisbenzyloxycarbonylguanidino)phenyl]-propionate as a white solid. $^1$H-NMR (200 MHz, CDCl$_3$): 2.86 (m, 2H), 3.60 (s, 3H), 5.17 (m, 7H), 7.09 (d, 1H), 7.35 (m, 17H), 7.65 (d, 2H), 10.26 (s, br, 1H), 11.90 (s, br, 1H). MS (ESI): 639 (M+H)$^+$.

A solution of 500 mg (0.78 mmol) of compound H, methyl benzyloxycarbonylamino-3-[3-(N,N'-bisbenzyloxycarbonylguanidino)phenyl]propionate, in 7 ml of THF and 3.5 ml of water is admixed with 66 mg (1.56 mmol) of lithium hydroxide monohydrate. The mixture is heated at boiling point for 16 h, and the solvent is then removed under reduced pressure. The residue is partitioned between water and ethyl acetate. The phases are separated and the aqueous phase is then adjusted to pH 1 using concentrated hydrochloric acid. The aqueous phase is extracted twice with ethyl acetate, and the organic phase is dried over sodium sulphate and concentrated. The residue is chromatographed over silica gel (dichloromethane/ethyl acetate gradient). This gives 3-(benzyloxycarbonylamino)-3-[3-(N-benyloxycarbonyl-guanidino)phenyl]-propionic acid (I) (270 mg, 70%) as a colourless oil. $^1$H-NMR (400 MHz, CD$_3$OD): 2.78 (m, 2H), 5.05 (s, 2H), 5.11 (m, 1H), 5.31 (s, 2H), 7.37 (m, 14H). MS (ESI): 491 (M+H)$^+$.

At 23° C., a solution of 20 mg (0.108 mmol) of (5R,S)-3,4,5,6-tetrahydro-5-methylamino-2-ureidopyrimidin-4-one, 53 mg (0.108 mmol) of the acid I,40 mg (0.216 mmol) of O-(7-azabenzotriazol-1-yl)-1,1,3,3-tetramethyluronium hexafluoro-phosphate (HATU) and 26 mg (0.216 mmol) of diusopropylethylamine in 5 ml of DMF is stirred for 16 h. The solvent is then removed under reduced pressure. The residue is stirred with 2 M hydrochloric acid. The aqueous phase is decanted off from the residue. The residue is taken up in dichloromethane. The organic phase is extracted twice with 2 M hydrochloric acid, dried using sodium sulphate and concentrated under reduced pressure. This gives 70 mg (98%) of the coupling product as a white solid [MS (ESI): 658 (M+H)$^+$]. This is dissolved in 10 ml of methanol. The solution is admixed with 38 mg (0.213 mmol) of palladium (II) chloride and stirred under an atmosphere of hydrogen (atmospheric pressure) for 4 h. The solution is filtered and concentrated under reduced pressure. The residue is triturated with diethyl ether. The ether is decanted off and the residue is dried under reduced pressure, giving the title compound as a colourless oil (28 mg, 57%). $^1$H-NMR (400 MHz, CD$_3$OD): 2.81–3.34 (m, 7H), 3.86+3.99 (m, 1H), 4.77+5.16 (m, 1H), 7.35–7.62 (m, 4H). MS (ESI) 390 (M+H)$^+$.

Example 3

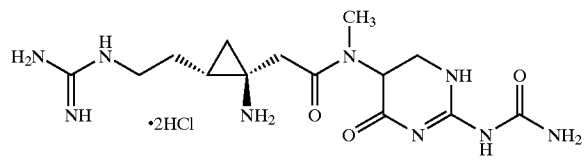

5-{N-Methyl-N-2'-[1-amino-2-(2-guanidinoethyl) cyclopropyl]acetamino}-5,6-dihydro-2-ureido-4 (1H)-pyrimidone Dihydrochloride The reactions are carried out in accordance with scheme 2 above, and the compounds are referred to as J to S, in accordance with scheme 2.

At 0° C., a solution of 62.9 g (185 mmol) of J, 2-(2-benzyloxyethyl)-1-chloro-1-(1,2,2-trichlorovinyl) cyclopropane, in 50 ml of anhydrous methanol is slowly added dropwise with stirring to a freshly prepared solution of 34.0 g of sodium (1.48 mol, 8 equivalents) in 250 ml of methanol. The mixture is then heated at reflux for 2 d. After cooling to room temperature, the mixture is admixed with 700 ml of water and extracted with diethyl ether. The combined organic phases are concentrated under reduced pressure and the residue is taken up in 300 ml of methanol. 25 ml of 10 per cent hydrochloric acid are added and the reaction mixture is stirred for 45 min. The mixture is then admixed with 300 ml of saturated sodium bicarbonate solution and extracted with diethyl ether. The ether extracts are dried over calcium chloride. Removal of the solvent under reduced pressure gives a dark-brown oil. Filtration through 300 g of silica gel (PE:diethyl ether 10:1) gives 24.4 g (47%) of K methyl [2-(2-benzyloxyethyl)cyclo-propylidene]chloroacetate in the form of a pale yellow liquid as a mixture of two diastereomers in the ratio of 1:1.6.-$^{13}$C-NMR (62.9 MHz, CDCl$_3$, additionally DEPT), isomer A: δ=11.6 (–), 20.3 (+), 31.6 (–), 52.8 (+), 68.8 (–), 72.9 (–), 115.3 (C$_{quart}$), 127.49 (+), 127.53 (+), 128.3 (+), 138.3 (C$_{quart}$), 143.8 (C$_{quart}$), 162.4 (C$_{quart}$). -isomer B: δ=15.6 (–), 16.1 (+), 31.5 (–), 52.8 (+), 69.3 (–), 73.0 (–), 114.6 (C$_{quart}$), 127.49 (+), 127.53 (+), 128.3 (+), 143.3 (C$_{quart}$), 162–7 (C$_{quart}$). MS (70 eV), m/z (%): 280 (<1) [M$^+$], 245 (1) [M$^+$—Cl], 189 (2) [M$^+$—CH$_2$Ph], 91 (100) [CH$_2$Ph$^+$]. —C$_{15}$H$_{17}$ClO$_3$ (280.8): calc. C, 64.17 H, 6.10; found C, 63.24, H, 5.97.

A solution of 11.98 g (42.7 mmol) of K, methyl [2-(2-benzyloxyethyl)cyclo-propylidenelchloroacetate, in 100 ml of anhydrous methanol is slowly mixed with 8.42 g (42.7 mmol) of anhydrous N,N-dibenzylamine. The solution is stirred at room temperature for 16 h and then concentrated under reduced pressure. Column chromatography over 300 g of silica gel (PE:diethyl ether 9:1) gives 15.71 g (77%) of L, methyl (E)-2-[2-(benzyloxyethyl)-1-(N,N-dibenzyl-amino)cyclopropyl]-2-chloroacetate, (pale-yellow oil) as a mixture of two diastereomers in the ratio 1:1.6.-$^{13}$C-NMR (62.9 MHz, CDCl$_3$, additionally DEPT), isomer A: δ=23.6 (–), 29.2 (+), 29.4 (–), 51.1 (C$_{quart}$), 52.8 (+), 56.6 (–), 62.1 (+), 69.8 (–), 72.8 (–), 126.5 (+), 126.6 (+), 127.6 (+), 128.3 (+), 128.7 (+), 128.8 (+), 138.4 (C$_{quart}$), 139.7 (C$_{quart}$), 169.1 (C$_{quart}$). -isomer B: δ=23.2 (–), 26.0 (+), 29.5 (–), 50.4 (C$_{quart}$), 52.9 (+), 56.6 (–), 64.3 (+), 69.8 (–), 72.9 (–), 126.5 (+), 126.6 (+), 127.6 (+), 128.3 (+), 128.7 (+), 128.8 (+), 138.4 (C$_{quart}$), 139.0 (C$_{quart}$), 169.5 (C$_{quart}$). MS (70 eV), m/z (%): 442 (<1) [M$^+$—Cl], 386 (<1) [M$^+$—CH$_2$Ph], 91 (100) [CH$_2$Ph$^+$]. —C$_{29}$H$_{32}$ClNO$_3$ (478.0): calc. C, 72.87, H, 6.75; found C, 72.53, H, 6.84.

An autoclave is charged with 100 ml of methanol and about 2.00 g of palladium on activated carbon (10% strength, 50% water), flushed repeatedly with hydrogen and stirred at 4.5 bar for 30 min. A solution of 8.86 g (18.5 mmol) of L, methyl (E)-2-[2- (benzyloxyethyl)-1-(N,N-dibenzylamino)cyclopropyl]-2-chloroacetate, in 100 ml of methanol is added to the activated catalyst, and the mixture is stirred at 4.5 bar and room temperature for 7 days. The catalyst is then separated off by filtration through Celite and the filtrate is concentrated under reduced pressure. The residue is suspended in 110 ml of saturated sodium carbonate solution and, with vigorous stirring and in an ice-bath, admixed with 4.51 g (1.43 equivalents) of benzyl chloroformate and stirred at the same temperature for 5 h. Following extraction with ethyl acetate and drying over magnesium sulphate, the product is purified by column chromatography over silica Igel (diethyl ether). This gives 3.73 g (66%) of N, methyl (E)-2-[1-amino-2-(hydroxyethyl)cyclo-propyl]acetate hydrochloride. -$^1$H-NMR (250 MHz, CDCl$_3$): δ=0.39 (m$_c$, 1H), 1.00–1.30 (m, 3H), 1.9–02.00 (m, 1H), 2.18 (d, J$^2$=17.3 Hz, 1H,), 3.02 (d, J$^2$=17.3 Hz, 1H), 3.66 (s, 3H), 3.74 (m$_c$, 2H), 5.05 (m$_c$, 2H), 5.92 (s, 1H), 7.31 (m$_c$, 5H). -$^{13}$C-NMR (62.9 MHz, CDCl$_3$, additionally DEPT): δ=18.0 (–), 24.4 (+), 32.1 (–), 33.6 (C$_{quart}$), 37.4 (–), 51.5 (+), 61.9 (–), 66.9 (–), 128.0 (+), 128.1 (+), 128.4 (+), 136.0 (C$_{quart}$), 157.1 (C$_{quart}$), 172.6 (C$_{quart}$). -MS (70 eV), m/z (%): 307 (<1) [M$^+$], 276 (<1) [M$^+$—OCH$_3$], 172 (8) [M$^+$—OCOCH$_2$Ph], 91 (100) [CH$_2$Ph$^+$].

A solution of 1.600 g (5.209 mmol) of N, methyl (E)-2-[1-amino-2-(hydroxyethyl)cyclopropyl]-acetate hydrochloride, in 40 ml of dry dichloromethane is cooled to 0° C., admixed with 1.02 g (2.0 equivalents) of triethylamine and 1.19 g (2.0 equivalents) of methanesulphonate chloride and stirred at the same temperature for 2 h. The solvent is removed under reduced pressure and the residue is taken up in 50 ml of ethyl acetate and washed with 40 ml of NaHCO$_3$ soln. The aqueous phase is extracted with ethyl acetate. The organic phases are dried over magnesium sulphate and the solvent is removed under reduced pressure, giving 2.010 g (quantitative) of O, methyl (E)-2-[1-benzyloxycarbonylamino-2-(hydroxyethyl)cyclopropyl]-acetate, in the form of a slightly yellowish solid. -$^1$H-NMR (250 MHz, CDCl$_3$): δ=0.48 (m$_c$, 1H), 1.05–1.20 (m, 2H), 1.65–1.90 (m, 2H), 2.52 (d, 1H), 2.60 (d, 1H), 2.99 (s, 3H), 3.65 (s, 3H), 4.35 (m$_c$, 2H), 5.02 (s, 2H), 5.68 (s, 1H), 7.30 (m$_c$, 5H). —C$_{17}$H$_{23}$NO$_7$S (385.4): calc. C, 52.98, H, 6.01; found C, 53.08, H, 6.00.

2.010 g (5.209 mmol) of O, methyl (E)-2-[1-benzyloxycarbonylamino-2-hydroxyethyl)cyclopropyl]-acetate, are dissolved in 10 ml of dry DMF, admixed with 1.69 g (5.0 equivalents) of sodium azide and stirred at room temperature for 4 d. The solvent is removed under reduced pressure and the residue is then admixed with 100 ml of water and extracted twice with ethyl acetate, the extract is dried over sodium sulphate and the solvent is removed under reduced pressure. Column chromatography over silica gel (PE:diethyl ether 1:1→DE) gives 1.540 g (89%) of P, methyl (E)-2-[2-(azidoethyl)-1-(benzyloxycarbonylamino)cyclopropyl]acetate in the form of a colourless oil. -$^1$H-NMR (250 MHz, CDCl$_3$): δ=0.48 (m$_c$, 1H), 1.05–1.26 (m, 2H), 1.49 (m$_c$, 1H,), 1.75 (m$_c$, 1H), 2.54 (d, J$^2$=17 Hz, 1H), 2.69 (d, J$^2$=17 Hz, 1H), 3.42 (m$_c$, 2H), 3.68 (s, 3H), 5.05 (s, 2H), 5.60 (br. s, 1H), 7.33 (m$_c$, 5H). -$^{13}$C-NMR (62.9 MHz, CDCl$_3$, additionally DEPT): δ=19.3 (–), 23.2 (+), 29.2 (–), 33.5 (C), 36.6 (–), 50.8 (–), 51.8 (+), 66.5 (–), 128.0 (+), 128.5 (+), 128.5 (+), 136.2 (C$_{quart}$), 155.8 (C$_{quart}$), 172.3 (C$_{quart}$). -MS (DCI, NH$_3$), m/z (%): 350 (100) [M$^+$+NH$_4$], 333 (10) [M$^+$+H]. —C$_{16}$H$_{20}$N$_4$O$_4$ (332.4): calc. C, 57.82, H, 6.07; found C, 57.54, H, 5.87.

At room temperature, a solution of 1.51 g (4.54 mmol) of P, methyl (E)-2-[2-(azidoethyl)-1-(benzyloxycarbonylamino)-cyclopropyl]acetate, in 5 ml of THF is admixed with 1.19 g (1.0 equivalents) of triphenylphosphine and 82 μl (4.54 mmol) of water and stirred for 24 h. The solvent is removed under reduced pressure. 10 ml of a mixture of PE:diethyl ether=1:1 are added to the residue, and the mixture is treated in an ultrasonic bath until triphenylphosphine oxide precipitates out. The latter is filtered off and washed repeatedly with a total of 100 ml of the solvent mixture. The filtrate is concentrated under reduced pressure and the residue is then dissolved in 15 ml of DMF and admixed with 1.63 g (1.0 equivalents) of N,N'-bis (benzyloxycarbonyl) S-methyl isothiourea, 1.23 g (1.0 equivalents) of mercury(II) chloride and 0.92 g (2.0 equivalents) of triethylamine. After 2 h of stirring, the mixture is filtered through Celite, which is then washed with 150 ml of diethyl ether. The solvents are removed under reduced pressure and the residue is then taken up in 200 ml of dichloromethane and washed with 100 ml of water. Following drying over magnesium sulphate, the product is purified by column chromatography over silica gel (diethyl ether). This gives 1.82 g (65%) of R, methyl (E)-2-{2-[N,N'-(bisbenzyloxycarbonyl)guanidino]ethyl-1-(benzyloxycarbonyl-amino)cyclopropyl]acetate in the form of a glass-like oil. -$^1$H-NMR (250 MHz, CDCl$_3$): δ=0.48 (m$_c$, 1H), 1.11 (m$_c$, 2H), 1.63 (m$_c$, 2H), 2.52 (d, J$^2$=17.3 Hz, 1H), 2.74 (d, J$^2$=17.3 Hz, 1H), 3.40–3.80 (m, 2H), 3.66 (s, 3H), 5.05–5.20 (m, 6H), 5.69 (s, 1H), 7.2–7.4 (m, 15H), 8.61 (br. s, 1H), 11.75 (br. s, 1H). -$^{13}$C-NMR (62.9 MHz, CDCl$_3$): δ=19.2, 23.6, 28.8, 33.2, 36.7, 40.5, 51.6, 66.4, 67.0, 67.9, 127.7–128.6 (9×C), 134.5, 136.2, 136.7, 153.5, 155.8, 163.6, 172.4. —C$_{33}$H$_{36}$N$_4$O$_8$ (616.7): calc. C, 64.27, H, 5.88; found C, 64.57, H, 6.07.

At room temperature, a solution of 300 mg (0.486 mmol) of R, methyl (E)-2-{2-[N,N'-(bisbenzyloxycarbonyl)-guanidino]ethyl-1-(benzyloxycarbonylamino)cyclo-propyl] acetate in 6 ml of dioxane is admixed with 5 ml of 2 N aqueous sodium hydroxide solution. After 1 h, the mixture is diluted with 50 ml of water and extracted with 50 ml of ethyl acetate. By addition of 1 M hydrochloric acid and using a pH meter (glass electrode), the mixture is acidified to pH=5.4 and extracted with dichloromethane. Both organic extracts are, separately, washed with in each case 30 ml of saturated ammonium carbonate solution and then combined and dried over magnesium sulphate. Removal of the solvent under reduced pressure gives S (E)-2-{2-[N,N'-(bisbenzyloxycarbonyl)-guanidino]ethyl-1-(benzyloxycarbonylamino)-cyclopropyl]acetic acid as an oil. -$^1$H-NMR (250 MHz, CDCl$_3$): δ=0.46 (m$_c$, 1H), 1.09 (m$_c$, 2H), 1.61 (m$_c$, 2H), 2.53 (d, J$^2$=17 Hz, 1H), 2.75 (d, J$^2$=17 Hz, 1H), 3.4–3.8 (m, 2H), 5.05–5.20 (m, 6H), 5.83 (s, 1H), 7.2–7.5 (m, 15 H), 8.60 (s, 1H), 8.97 (s, 1H), 11–12 (br. S, 1H). -FAB-MS (glycerol matrix), m/z (%): 625 (20) [M$^+$+Na], 603 (45) [M$^+$+H].

The coupling of (5R,S)-3,4,5,6-tetrahydro-5-methylamino-2-ureidopyrimidin-4-one and acid S (E)-2-{2-[N,N'-(bisbenzyloxycarbonyl)guanidino]ethyl-1-(benzyloxycarbonyl-amino)-cyclopropyl]acetic acid and subsequent removal of the benzyloxycarbonyl protective groups is carried out as described in Example 1. The title compound is obtained as an amorphous solid (mixture of diastereomers). -$^1$H-NMR (250 MHz, D$_2$O): 0.88 (m, 1H), 0.93 (m, 1H), 1.05 (m, 1H), 1.12 (m, 2H), 2.81–3.02 (m, 5H), 3.07 (m, 2H), 3.92 (m, 2H), 4.95 (m, 1H).

J 2-(2-benzyloxyethyl)-1-chloro-1-(1,2,2-trichlorovinyl) cyclopropane was prepared according to: M. Es-Sayed, *PhD-thesis*, University of Hamburg 1992. -M. Kordes, *Diploma thesis*, University of Göttingen 1996.

Example 4

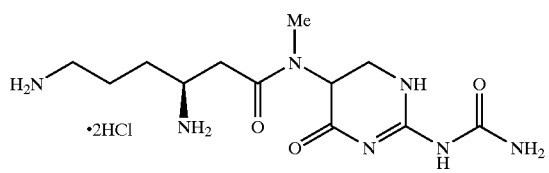

(3'S,5R,S)-5-[N-Methyl-N-(3',6'-diaminohexanoyl) amino]-5,6-dihydro-2-ureido-4(1H)-pyrimidone Dihydrochloride A solution of 1.0 g (2.6 mmol) of (3S)-3-benzyloxycarbonylamino-6-tert-butyloxy-carbonylaminohexanoic acid and 5 ml of a 4 M solution of hydrogen choride in dioxane is stirred at 23° C. for 30 min. The volatile components are removed under reduced pressure. This gives an oily residue which is reacted further without purification.

100 mg of the residue are suspended in 3 ml of dichloromethane. 34 mg (0.316 mmol) of chlorotrimethylsilane are added. The resulting solution is heated at 40° C. for 1 h and then cooled to 0° C. and admixed successively with 45 mg (0.474 mmol) of benzyl chloroformate and 80 mg (0.789 mmol) of triethylamine. The mixture is heated at 40° C. for 1 h. 0.7 ml of methanol are then added. The mixture is stirred at 23° C. for 10 min, and the volatile components are then removed under reduced pressure. The residue is taken up in dichloromethane. By washing the organic phase with 2 M hydrochloric acid, drying of the organic phase with sodium sulphate and removal of the solvent, the residue is digested with diethyl ether. Filtering off and drying under reduced pressure gives 100 mg of (3S)-3,6-bis-(benzyloxycarbonylamino)hexanoic acid as a white solid. $^1$H-NMR (200 MHz, DMSO): 1.41 (m, 4H), 2.33 (d, 2H), 2.95 (m, 2H), 3.78 (m, 1H), 5.02 (s, 2 H), 7.22 (m, 2H), 7.33 (m, 5 H). MS (DCI/NH$_3$): 432 (M+NH$_4$)$^+$.

The coupling of (5R,S)-3,4,5,6-tetrahydro-5-methylamino-2-ureidopyrimidin-4-one and (3S)-3,6-bis (benzyloxycarbonylamino)hexanoic acid and the subsequent removal of the benzyloxycarbonyl protective groups is carried out as described in Example 1. The title compound is obtained as an amorphous solid. $^1$H-NMR (400 MHz, D$_2$O): 0.88 (m, 1H), 0.93 (m, 1H), 1.05 (m, 1H), 1.12 (m, 2H), 2.81–3.02 (m, 5H), 3.07 (m, 2H), 3.92 (m, 2H), 4.95 (m, 1H).

Example 5

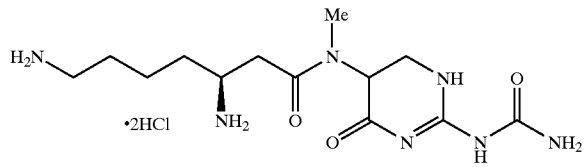

(3'S,5R,S)-5-[N-Methyl-N-(3',7'-diaminoheptanoyl) amino]-5,6-dihydro-2-ureido-4(1H)-pyrimidone Dihydrochloride The coupling of 86 mg (0.47 mmol) of (5R,S)-3,4,5,6-tetrahydro-5-methylamino-2-ureidopyrimidin-4-one and 200 mg (0.47 mmol) of (3S)-3,7-bis(benzyloxycarbonyl-amino)heptanoic acid and subsequent removal of the benzyloxycarbonyl protective groups is carried out as described in Example 1. The title compound is obtained as a white solid (57 mg, 30%). $^1$H-NMR (400 MHz, CD$_3$OD): 1.55 (m, 2H), 1.74 (m, 4H), 2.75 (m, 1H), 2.96 (m, 3H), 3.14 (m, 3H), 3.58 (m, 1H), 3.89 (m, 1H), 4.01 (m, 1H), 5.14 (m, 1H).

Example 6

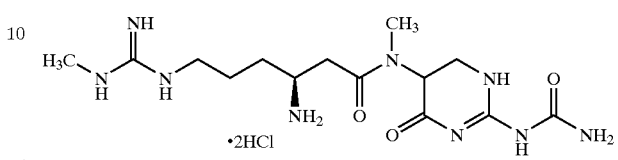

(3'S,5R,S)-5-{N-Methyl-N-[3'-amino-6'-(N'-methylguanidino)hexanoyl]amino}-5,6-dihydro-2-ureido-4(1H)-pyrinidone Dihydrochloride At room temperature, a solution of 450 mg (1.1 mmol) of 2'-trimethylsilylethyl (3S)-6-amino-3-benzyloxycarbonylhexanoate and 400 mg (1.1 mmol) of N,N'-dibenzyl-oxycarbonyl-N-methyl S-methyl isothiourea in 10 ml of DMF is admixed with 0.75 ml (5.37 mmol) of triethylamine and 320 mg (1.2 mmol) of mercury(II) chloride. The mixture is stirred at room temperature for 17 h, precipitated white solid is filtered off and the volatile components are removed under reduced pressure. The residue is chromatographed over silica gel (dichloromethane:ethyl acetate 10:1 to 3:1). This gives 470 mg (62%) of 2'-trimethylsilylethyl (3S)-3-benzyloxycarbonyl-6-[N,N'-bis-(benzyloxycarbonyl)-N-methylguanidino]hexanate as a colourless oil. MS (ESI): 705 (M+H)$^+$. This product is dissolved in 10 ml of THF and, at room temperature, admixed with a solution of 421 mg (1.3 mmol) of tetrabutylammonium fluoride trihydrate in 20 ml of THF. The mixture is stirred at room temperature for 2 h, and 50 ml of diethyl ether and 20 ml of 2 M hydrochloric acid are added. The phases are separated and the aqueous phase is extracted with diethyl ether. The combined organic phases are dried over Na$_2$SO$_4$. Removal of the solvent under reduced pressure gives 250 mg (62%) of (3S)-3-benzyloxycarbonyl-6-[N,N'-bis(benzyloxycarbonyl)-N-methylguanidino] hexanoic acid as a colourless oil. MS (ESI): 605 (M+H)$^+$.

The coupling of 76.5 mg (0.41 mmol) of (5R,S)-3,4,5,6-tetrahydro-5-methylamino-2-ureidopyrimidin-4-one with the acid described and the subsequent removal of the benzyloxycarbonyl protective groups is carried out as described in Example 1. The title compound is obtained as a beige solid (180 mg, 99%). $^1$H-NMR (400 MHz, CD$_3$OD): 1.70 (m, 4H), 2.72–2.94 (m, 2H), 2.84 (s, 3H), 3.14 (s, 3H), 3.23 (m, 2H), 3.61 (m, 1H), 3.90 (m, 1H), 4.02 (dt, 1H), 5.15 (m, 1H).

Example 7

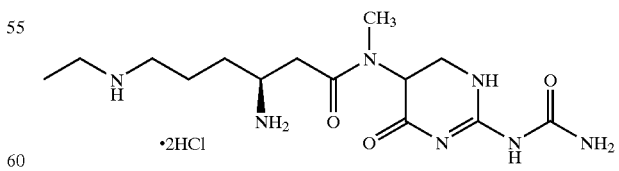

(3'S,5R,S)-5-[N-Methyl-N-(3'-amino-6'-ethylaminohexanoyl)amino]-5,6-dihydro-2-ureido-4 (1H)-pyrimidone Dihydrochloride 1000 mg (3.0 mmol) of methyl (3S)-6-amino-3-benzyloxycarbonylaminohexanoate are initially charged in 5 ml of 1,2-dichloroethane and, at room temperature, admixed with 250 μl (4.5 mmol) of acetaldehyde and 190 μl of acetic acid. The mixture is stirred at room temperature for 30 min and cooled to 0° C., and 1601 mg (7.6 mmol) of sodium triacetoxyborohydride are added. The mixture is stirred at room temperature for 20 h, diluted with 30 ml of dichloromethane and extracted with 1 M hydrochloric acid. The aqueous phase is adjusted to pH 9 using sodium bicarbonate solution and extracted three times with in each case 30 ml of ethyl acetate. The combined organic phases are dried using $Na_2SO_4$ and the solvent is distilled off under reduced pressure. This gives 640 mg (66%) of methyl (3S)-3-benzyloxycarbonylamino-6-ethylaminohexanoate as a colourless oil. $^1$H-NMR (200 MHz, DMSO): 0.97 (t, 3H), 1.37 (m, 4H), 2.42 (m, 6H), 3.56 (s, 3H), 3.78 (m, 1H), 5.02 (s, 2H), 7.35 (m, 6H). MS (DCI/$NH_3$): 323 (M+H)$^+$.

The product described (630 mg, 1.95 mmol) is dissolved in 10 ml of dichloromethane and, at 0° C., admixed with 300 μl (2.15 mmol) of triethylamine and 310 μl (2.15 mmol) of benzyl chloroformate. The mixture is stirred at room temperature for 16 h, the organic phase is washed twice with water and dried over $Na_2SO_4$ and the solvent is removed under reduced pressure. The residue is chromatographed over silica gel (ethyl acetate/cyclohexane 1:1). This gives 515 mg (58%) of methyl (3S)-3-benzyloxycarbonylamino-6-[(benzyloxycarbonyl)ethyl-amino]hexanoate as a white solid. $^1$H-NMR (200 MHz, DMSO): 1.02 (t, 3H), 1.40 (m, 4H), 2.42 (m, 2H), 3.18 (m, 4H), 3.56 (s, 3H), 3.82 (m, 1H), 5.01 (s, 2H), 5.06 (s, 2H), 7.25 (m, 1H), 7.35 (m, 10H). MS (ESI): 457 (M+H)$^+$.

The product described (510 mg, 1.12 mmol) is dissolved in 4 ml of dichloromethane and, at room temperature, mixed with 158 mg (1.30 mmol) of potassium trimethylsilanolate. The mixture is stirred at room temperature for 16 h, diluted with 20 ml of dichloromethane and washed with 1 M of hydrochloric acid, the organic phase is dried over $Na_2SO_4$ and the volatile components are removed under reduced pressure. This gives 463 mg (94%) of (3S)-3-benzyloxycarbonylamino-6-[(benzyloxycarbonyl)-ethyl]aminohexanoic acid as a white solid. $^1$H-NMR (200 MHz, DMSO): 1.02 (t, 3H), 1.40 (m, 4H), 2.35 (m, 2H), 3.20 (m, 4H), 3.81 (m, 1H), 5.00 (s, 2H), 5.05 (s, 2H), 7.25 (m, 1H), 7.33 (m, 10H). MS (ESI): 443 (M+H)$^+$.

The coupling of 42 mg (0.27 mmol) of (5R,S)-3,4,5,6-tetrahydro-5-methylamino-2-ureidopyrimidin-4-one and 100 mg (0.27 mmol) of the acid described and the subsequent removal of the benzyloxycarbonyl protective groups is carried out as described in Example 1. The title compound is obtained as a white solid (60 mg, 64%). $^1$H-NMR (400 MHz, $CD_3OD$): 1.32 (t, 3H), 1.83 (m, 4H), 2.80 (dd, 1H), 2.95–3.18 (m, 5H), 3.19 (s, 3H), 3.61 (m, 1H), 3.90 (ddd, 1H), 4.03 (dt, 1H), 5.18 (m, 1H). MS (ESI): 342 (M+H)$^+$.

Example 8

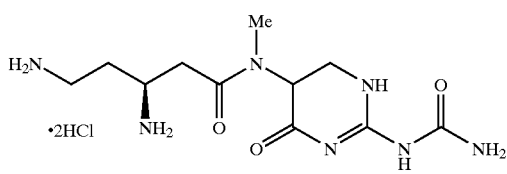

(3'S,5R,S)-5-[N-Methyl-N-(3',5'-diaminopentanoyl)amino]-5,6-dihydro-2-ureido-4(1H)-pyrimidone Dihydrochloride The coupling of 46 mg (0.25 mmol) of (5R,S)-3,4,5,6-tetrahydro-5-methylamino-2-ureidopyrimidin-4-one and 100 mg (0.25 mmol) of (3S)-3,5-bis-(benzyloxycarbonylamino)pentanoic acid and the subsequent removal of the benzyloxycarbonyl protective groups is carried out as described in Example 1. The title compound is obtained as a white solid. (25 mg, 27%). $^1$H-NMR (400 MHz, $CD_3OD$): 2.10 (m, 2H), 2.86 (dd, 1H), 3.04 (m, 1H), 3.10 (dd, 2H), 3.18 (s, 3H), 3.72 (m, 1H), 3.89 (ddd, 1H), 4.02 (dt, 1H), 5.19 (m, 1H).

Example 9

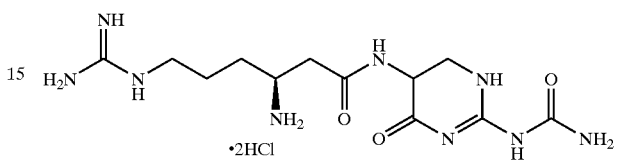

(3'R,5R,S)-5-[N-(3'-amino-6'-guanidinohexanoyl)amino]-5,6-dihydro-2-ureido-4(1H)-pyrimidone Dihydrochloride The preparation of the title compound and the required component (5R,S)-3,4,5,6-tetrahydro-5-amino-2-ureidopyrimidin-4-one were carried out analogously to published syntheses (cf. V. V. Sokolov, S. I. Kozhushkov, S. Nikolskaya, V. N. Belov, M. Es-Sayed, A. de Meijere, *Eur. J. Org. Chem.* 1998, 777). $^1$H-NMR (200 MHz, $D_2O$): 1.45–1.65 (m, 4H), 2.55–2.70 (m, 2H), 3.05–3.13 (m, 2H), 3.55 (m, 1H), 3.62 (dd, 1H), 3.71 (dd, 1H), 4.87 (dd, 1H).

Example 10

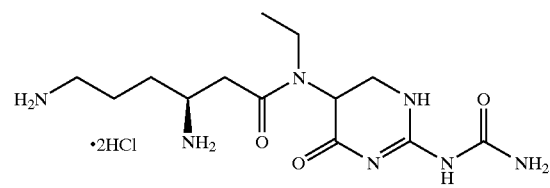

(3'S,5R,S)-5-[N-Ethyl-N-(3',6'-diaminohexanoyl)amino]-5,6-dihydro-2-ureido-4(1H)-pyrimidone Dihydrochloride The coupling of 120 mg (0.60 mmol) of (5R,S)-3,4,5,6-tetrahydro-5-ethylamino-2-ureidopyrimidin-4-one (synthesized analogously to the methyl compound: cf. V. V. Sokolov, S. I. Kozhushkov, S. Nikolskaya, V. N. Belov, M. Es-Sayed, A. de Meijere, *Eur. J. Org. Chem.* 1998, 777) and 250 mg (0.60 mmol) of (3S)-3,6-bis-(benzyloxycarbonylamino)hexanoic acid and the subsequent removal of the benzyloxycarbonyl protective groups are carried out as described in Example 1. The title compound is obtained as an amorphous solid (115 mg, 48%). $^1$H-NMR (400 MHz, $CD_3OD$): 1.26 (t, 3H), 1.78 (m, 4H), 2.62–2.90 (m, 2H), 2.98 (m, 2H), 3.49 (m, 1H), 3.63 (m, 2H), 3.89 (m, 1H), 4.08 (m, 1H), 4.62 (m, 1H). MS (ESI): 328 (M+H)$^+$.

Example 11

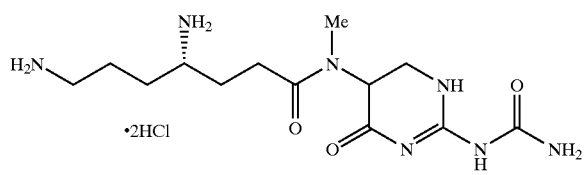

(4'S,5R,S)-5-[N-Methyl-N-(4',7'-diaminoheptanoyl)
amino]-5,6-dihydro-2-ureido-4(1H)-pyrimidone
Dihydrochloride (4S)4,7-Bis-(benzyloxycarbonylamino)heptanoic acid was synthesized from (3S)-3,6-bis-(benzyloxycarbonylamino)hexanoic acid (cf. Example 4) analogously to a literature example (H. M. M. Bastiaans, A. E. Alewijnse, J. L. van der Baan, H. C. J. Ottenheijm, *Tetrahedron Lett.* 1994, 35, 7659). The coupling of 22 mg (0.12 mmol) of (5R,S)-3,4,5,6-tetrahydro-5-methylamino-2-ureidopyrimidin-4-one and 50 mg (0.12 mmol) of the corresponding acid and the subsequent removal of the benzyloxycarbonyl protective groups are carried out as described in Example 1. The title compound is obtained as a white solid (25 mg, 52%). MS (ESI): 328 (M+H)+.

Example 12

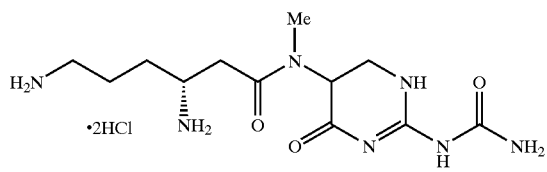

(3'R,5R,S)-5-[N-Methyl-N-(3',6'-diaminohexanoyl)
amino]-5,6-dihydro-2-ureido-4(1H)-pyrimidone
Dihydrochloride The coupling of 112 mg (0.60 mmol) of (5R,S)-3,4,5,6-tetrahydro-5-methylamino-2-ureidopyrimidin-4-one and 250 mg (0.60 mmol) of (3R)-3,6-bis-(benzyloxycarbonylamino)hexanoic acid and the subsequent removal of the benzyloxycarbonyl protective groups are carried out as described in Example 1. The title compound is obtained as a beige solid (204 mg, 88%). $^1$H-NMR (400 MHz, CD$_3$OD): 1.78 (m, 4H), 2.80 (m, 2H), 2.96 (m, 2H), 3.17 (s, 3H), 3.62 (m, 1H), 3.92 (m, 1H), 4.03 (n, 1H), 5.18 (m, 1H).

Example 13

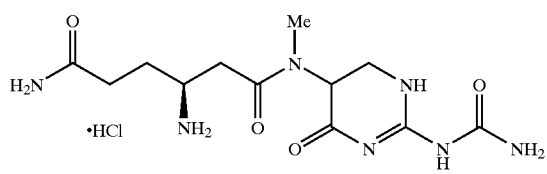

(3'R,5R,S)-5-[N-Methyl-N-(3'-amino-5'-carbamoyl-
pentanoyl)amino]-5,6-dihydro-2-ureido-4(1H)-
pyrimidone Dihydrochloride The coupling of 157 mg (0.85 mmol) of (5R,S)-3,4,5,6-tetrahydro-5-methylamino-2-ureidopyrimidin-4-one and 250 mg (0.85 mmol) of (3R)-3-(benzyloxycarbonyl-amino)-5-carbamoylpentanoic acid and the subsequent removal of the benzyloxycarbonyl protective groups are carried out as described in Example 1. The title compound is obtained as a beige solid (81 mg, 26%). $^1$H-NMR (400 MHz, CD$_3$OD): 1.94 (m, 2H), 2.45 (m, 2H), 2.72 (m, 1H), 2.91 (m, 1H), 3.09 (s, 3H), 3.61 (m, 1H), 3.78 (ddd, 1H), 3.94 (m, 1H), 5.15 (m, 1H).

Example 14

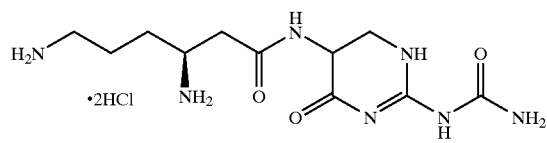

(3'R,5R,S)-5-[N-(3',6'-Diaminohexanoyl)amino]-5,6-
dihydro-2-ureido-4(1H)-pyrimidone
Dihydrochloride The coupling of 62 mg (0.36 mmol) of (5R,S)-3,4,5,6-tetrahydro-5-amino-2-ureido-pyrimidin-4-one (cf. Example 10) and 150 mg (0.36 mmol) of (3S)-3,6-bis-(benzyloxycarbonylamino)hexanoic acid and the subsequent removal of the benzyloxy-carbonyl protective groups are carried out as described in Example 1. The title compound is obtained as a white solid (110 mg, 82%). $^1$H-NMR (400 MHz, CD$_3$OD): 1.82 (m, 4H), 2.75 (dd, 1H), 2.80 (dd, 1H), 2.99 (m, 2H), 3.62 (m, 1H), 3.78 (m, 1H), 3.94 (m, 1H), 5.02 (m, 1H).

Example 15

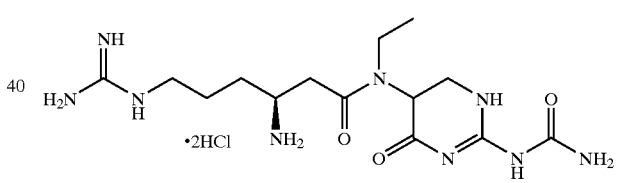

(3'S,5R,S)-5-[N-Ethyl-N-(3'-amino-6'-
guanidinohexanoyl)amino]-5,6-dihydro-2-ureido-4
(1H)-pyrimidone Dihydrochloride The synthesis of (5R,S)-3,4,5,6-tetrahydro-5-ethylamino-2-ureidopyrimidin-4-one and the reaction of this building block with (3S)-1-diazo-3-benzyloxycarbonyl-6-[N,N'-bis-(benzyloxycarbonyl)guanidino]hexan-2-one are carried out analogously to a published procedure (cf. V. V. Sokolov, S. I. Kozhushkov, S. Nikolskaya, V. N. Belov, M. Es-Sayed, A. de Meijere, *Eur. J. Org. Chem.* 1998, 777). The starting material used is N-ethyl-DL-asparagine (Y. Liwschitz, Y. Edlitz-Pfeffermann, Y. Lapidoth, *J. Am. Chem. Soc.* 1956, 78, 3069). The subsequent removal of the benzyloxycarbonyl protective groups is carried out as described for Example 1. The title compound is obtained as a white solid: melting point: 170–172° C. $^1$H-NMR (250 MHz, D$_2$O): 1.03 (t, 3H), 1.35–1.55 (m, 4H), 2.25–2.45 (m, 2H), 2.95–3.05 (m, 2H), 3.30–3.77 (m, 5H), 4.42 (m, 1H). MS (FAB): 370 (M+H)+.

Example 16

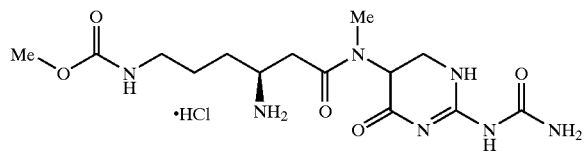

(3'S,5R,S)-5-[N-Methyl-N-(3'-amino-6'-methoxycarbonylaminohexanoyl)-amino]-5,6-dihydro-2-ureido-4(1H)-pyrimidone Hydrochloride The coupling of 104 mg (0.56 mmol) of (5R,S)-3,4,5,6-tetrahydro-5-methylamino-2-ureidopyrimidin-4-one and 190 mg (0.56 mmol) of (3S)-3-benzyloxycarbonylamino-6-methoxycarbonylaminohexanoic acid and the subsequent removal of the benzyloxycarbonyl protective group are carried out as described in Example 1. The title compound is obtained as a white solid (30 mg, 13%). $^1$H-NMR (400 MHz, CD$_3$OD): 1.58 (m, 2H), 1.69 (m, 2H), 2.65–3.07 (m, 4H), 3.14 (m, 3H), 3.57 (m, 1H), 3.63 (s, 3H), 3.88 (m, 1H), 4.03 (m, 1H), 5.18 (m, 1H). MS (ESI): 372 (M+H)$^+$.

Example 17

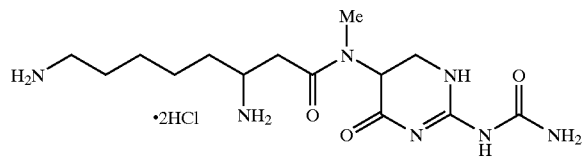

(3'R,S,5R,S)-5-[N-Methyl-N-(3',8'-diaminooctanoyl)amino]-5,6-dihydro-2-ureido-4(1H)-pyrimidone Dihydrochloride 3.70 g (14.7 mmol) of 6-benzyloxycarbonylamino-1-hexanol (S. Fernandez, E. Menendez, V. Gotar, *Synthesis* 1991, 713–716) and 14.9 g (147 mmol) of triethylamine are dissolved in 50 ml of dichloromethane. The solution is cooled to 0° C. and admixed with 7.03 g (44.2 mmol) of sulphur trioxide/pyridine complex in 44 ml of dimethyl sulphoxide. The mixture is then warmed to room temperature and stirred for 25 min. The solution is poured into 400 ml of ice-water and extracted repeatedly with diethyl ether. The combined organic phases are washed three times with 1 M hydrochloric acid and once each with water and saturated aqueous NaCl solution, dried over Na$_2$SO$_4$ and freed from the solvent under reduced pressure. The resulting colourless oil (3.50 g) is dissolved in 20 ml of THF (solution A). Separately, 3.54 g (16.9 mmol) of methyl diethylphosphonoacetate in 40 ml of THF are admixed, at 0° C., with 17 ml of a 1 M THF solution of sodium (bistrimethylsilyl)amide. The mixture is stirred for 45 min, and solution A is added at 0° C. The resulting solution is warmed to room temperature, stirred for 2 h and concentrated under reduced pressure. The residue is chromatographed over silica gel (ethyl acetate/cyclohexane 1:4 to 1:2). This gives 1.73 g (34%) of methyl (Z)-8-benzyloxycarbonylamino-2-octenecarboxylate as a colourless oil. $^1$H-NMR (200 MHz, DMSO): 1.17–1.49 (m, 6H), 2.18 (q, 2H), 2.95 (q, 2H), 3.66 (s, 3H), 5.00 (s, 2H), 5.87 (d, 1H), 6.89 (td, 1H), 7.25 (m, 1H), 7.34 (m, 5H). MS (DCI/NH$_3$): 323 (M+NH$_4$)$^+$.

0.88 g (2.9 mmol) of the ester is added to 9 ml of a solution of ethanol saturated with ammonia. In a closed vessel, the mixture is heated at 100° C. (bath temperature) for 6 h. After cooling to room temperature, the volatile components are removed under reduced pressure. The residue is taken up in 15 ml of dichloromethane. The resulting solution is cooled to 0° C. and admixed successively with 0.58 ml (4.2 mmol) of triethylamine and 0.51 ml (3.6 mmol) of benzyl chloroformate. The mixture is allowed to warm to room temperature and stirred for another 15 h. The mixture is diluted with 50 ml of dichloromethane and washed with 1 M of hydrochloric acid, the organic phase is dried over Na$_2$SO$_4$ and the volatile components are removed under reduced pressure. Chromatography of the residue over silica gel (ethyl acetate/cyclohexane 1:3 to 1:2) gives 194 mg (14%) of ethyl (3R,S)-3,8-bis(benzyloxycarbonylamino)octanoate [MS (ESI): 471 (M+H)$^+$] and 248 mg (19%) of methyl (3R,S)-3,8-bis(benzyloxycarbonylamino)octanoate [MS (ESI): 457 (M+H)$^+$] in the form of colourless oils. Both products are combined, dissolved in 10 ml of dichloromethane and admixed with 280 mg (1.9 mmol) of potassium trimethylsilanolate. The mixture is stirred at RT for 1 h, a further 100 mg of potassium trimethylsilanolate are added and stirring is continued for another hour. The mixture is diluted with 20 ml of dichloromethane, the organic phase is washed with 2 M hydrochloric acid and dried over Na$_2$SO$_4$ and the solvent is evaporated under reduced pressure. This gives 393 mg (93%) of (3R,S)-3,8-bis(benzyloxycarbonylamino)octanoic acid as a white solid. $^1$H-NMR (300 MHz, DMSO): 1.21 (m, 4H), 1.38 (m, 4H), 2.36 (m, 2H), 2.95 (q, 2H), 3.77 (m, 1H), 5.01 (s, 4H), 7.14 (m, 1H), 7.35 (m, 10H), 12.08 (s, 1H).

The coupling of 200 mg (0.45 mmol) of the acid thus prepared with 84 mg (0.45 mmol) of (5R,S)-3,4,5,6-tetrahydro-5-methylamino-2-ureidopyrimidin-4-one and the subsequent removal of the benzyloxycarbonyl protective groups are carried out as described in Example 1. The title compound is obtained as a white solid (175 mg, 94%). $^1$H-NMR (400 MHz, CD$_3$OD): 1.47 (m, 4H), 1.72 (m, 4H), 2.75 (m, 1H), 2.94 (m, 3H), 3.15 (m, 3H), 3.58 (m, 1H), 3.90 (m, 1H), 4.03 (m, 1H), 5.18 (m, 1H). MS (ESI): 342 (M+H)$^+$.

Example 18

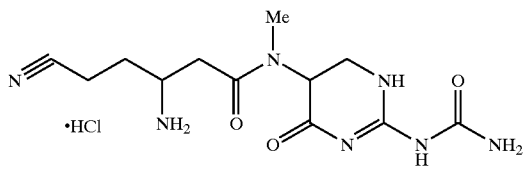

(3'R,S,5R,S)-5-[N-Methyl-N-(3'-amino-5'-cyanopentanoyl)amino]-5,6-dihydro-2-ureido-4(1H)-pyrimidone Hydrochloride A solution of 1.00 g (10.1 mmol) of the sodium salt of 3-cyanopropanoic acid in 50 ml of dichloromethane was extracted with 30 ml of a 1-molar hydrochloric acid. The organic phase was dried over magnesium sulphate and the solvent was distilled off using a rotary evaporator. The crude 3cyanopropanoic acid was freed of solvent residues under high vacuum.

The residue was taken up in 15 ml of THF and, at 0° C., admixed a little at a time with 1.96 g (12.1 mmol) of N,N-carbonyldiimidazole. The mixture was stirred at room temperature for one hour (solution A).

In a second flask, a solution of 960 mg (10.1 mmol) of magnesium chloride and 2.75 g (15.1 mmol) of the potassium salt of ethyl malonate in 25 ml of THF was heated at 50° C. for 4 hours. The mixture was cooled to room temperature and then admixed dropwise with the solution A which had been prepared earlier. The mixture was stirred at room temperature overnight.

The solvent was distilled off using a rotary evaporator and the residue was taken up in 20 ml of water and 50 ml of dichloromethane. The organic phase was filtered through kieselguhr and dried over sodium sulphate. The residue was purified over a flash column (silica gel, mobile phase cyclohexane/ethyl acetate 10:1 with increasing polarity to 1:1). This gave 617 mg (36%) of ethyl 5-cyano-3-oxopentanoate. $^1$H-NMR (300 MHz, DMSO) 1.19 (t, 3H), 2.60 (t, 2H), 2.95 (t, 2H), 3.62 (s, 2H), 4.10 (q, 2H). MS (EI): 169 (M)$^+$.

3.80 g (22.4 mmol) of ethyl 5-cyano-3-oxopentanoate were taken up in 5 ml of a saturated ethanolic ammonia solution and stirred at room temperature for 24 h. The volatile components were distilled off using a rotary evaporator, giving 3.60 g (95%) of ethyl 3-amino-5-cyano-2-pentenoate. $^1$H-NMR (300 MHz, DMSO) 1.16 (t, 3H), 2.37 (t, 2H), 2.75 (t, 2H), 3.99 (q, 2H), 4.41 (s, 1H), 6.96 (s, broad, 1H), 7.69 (s, broad, 1H). MS (DCI/NH$_3$): 169 (M+H)$^+$, 186 (M+NH$_4$)$^+$, 337 (2M+H)$^+$.

At 0° C., a solution of 50.0 mg (297 µmol) of ethyl 3-amino-5-cyano-2-pentenoate in 1 ml of methanol was added dropwise to a solution of 56.0 mg (892 µmol) of sodium cyanoborohydride in 1 ml of abs. methanol. The mixture was mixed with 6 drops of glacial acetic acid, the cooling bath was removed and the mixture was stirred at room temperature for 2 h.

The mixture was admixed with 1 ml of a sat. sodium bicarbonate solution and concentrated using a rotary evaporator. The aqueous phase was extracted twice with in each case 5 ml of dichloromethane. The organic phase was dried over sodium sulphate and the solvent was distilled off using a rotary evaporator. 39.9 mg (79%) of the desired ethyl 3-amino-5-cyanopentanoate remained. $^1$H-NMR (300 MHz, DMSO) 1.19 (t, 3H), 1.49 (m, 1H), 1.68 (m, 1H), 2.27 (dd, 1H), 2.40 (dd, 1H), 2.55 (t, 2H), 3.00 (m, 1H), 4.08 (q, 2H). MS (DCI/NH$_3$): 171 (M+H)$^+$.

At room temperature, a solution of 723 mg (3.31 mmol) of BOC anhydride in 0.5 ml of dioxane was added dropwise to a solution of 470 mg (2.76 mmol) of ethyl 3-amino-5-cyanopentanoate and 458 mg (3.31 mmol) of potassium carbonate in 10ml of dioxane/water (1:1). The volatile components were distilled off using a rotary evaporator and the residue was extracted twice with in each case 5 ml of dichloromethane. The organic phase was dried over sodium sulphate and the solvent was distilled off using a rotary evaporator. The crude product was purified over a flash column (silica gel, mobile phase:cyclohexane/ethyl acetate 20:1 with increasing polarity to 1:1). This gave 505 mg (68%) of ethyl 3-[(tert-butoxycarbonyl)amino]-5-cyanopentanoate. $^1$H-NMR (300 MHz, DMSO) 1.19 (t, 3H), 1.35 (s, 9H), 1.70 (m, 2H), 2.48 (m, 4H), 3.81 (m, 1H), 4.02 (q, 2H), 6.80 (m, 1H). MS (DCI/NH$_3$): 288 (M+NH)$^+$.

213 mg (1.66 mmol) of potassium trimethylsilanolate were added to a solution of 300 mg (1.11 mmol) of ethyl 3-[(tert-butoxycarbonyl)amino]-5-cyanopentanoate in 1 ml of dichloromethane, and the mixture was stirred at room temperature. After 2 hours, another 213 mg of potassium trimethylsilanolate were added, and the mixture was stirred for 30 min.

The mixture was admixed with 1 ml of a sat. ammonium chloride solution and extracted with 2 ml of dichloromethane. The aqueous phase was adjusted to pH 1 using 1-molar hydrochloric acid and extracted twice with in each case 3 ml of dichloromethane. The combined organic phases were dried over sodium sulphate and freed from the solvent using a rotary evaporator. This gave 177 mg (66%) of the desired 3-[(tert-butoxycarbonyl)amino]-5-cyanopentanoic acid. $^1$H-NMR (300 MHz, d$^6$-DMSO) 1.38 (s, 9H), 1.65 (m, 1H), 1.75 (m, 1H), 2.38 (m, 2H), 2.45 (m, 2H), 3.79 (m, 1H), 6.80 (d, 1H), 12.20 (s, broad, 1H). MS (DCI/NH$_3$): 260 (M+NH$_4$)$^+$.

The coupling of 15 mg (82 µmol) of 3-[(tert-butoxycarbonyl)amino]-5-cyano-pentanoic acid with (5R, S)-3,4,5,6-tetrahydro-5-methylamino-2-ureidopyrimidin-4-one was carried out as described in Example 1. The yield was 32%. To remove the BOC group, the crude product was taken up in 1 ml of 4 molar HCl in dioxane and stirred at room temperature for 30 min. All volatile components were distilled off using a rotary evaporator. The residue was taken up in methanol and admixed dropwise with acetone until a precipitate was formed. The supernatant was decanted off and the white solid that remained was freed from the solvent residues under oilpump vacuum. This gave 2.1 mg (28%) of the title compound. MS (DCI): 311 (M+H)$^+$.

What is claimed is:

1. Compounds of the formula:

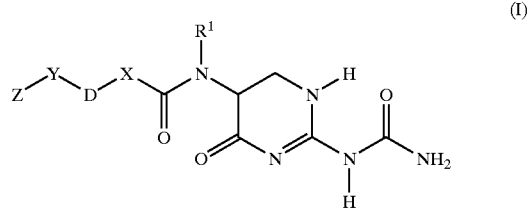

(I)

in which

R$^1$ represents hydrogen or (C$_1$–C$_6$)alkyl,

X represents a group of the formula —(CH$_2$)$_m$—, in which m is 1 or 2,

D is selected from groups of the formulae D$_1$ to D$_3$

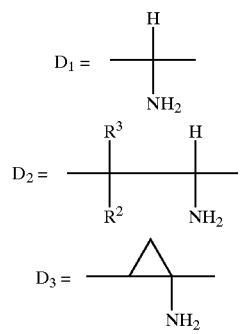

in which R$^2$ represents hydrogen or hydroxyl,

R$^3$ represents hydrogen, or

R$^2$ and R$^3$ together form an oxo group,

Y represents a straight-chain or branched (C$_1$–C$_5$) alkanediyl group which may optionally be substituted by hydroxyl or oxo, or represents a group of the formula below

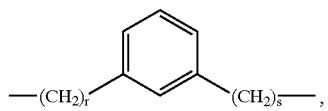

in which r and s are identical or different and are 0, 1 or 2,

Z represents a group selected from groups of the formulae

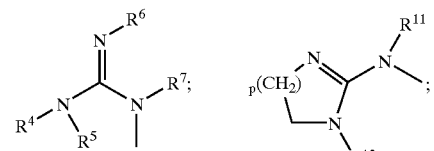

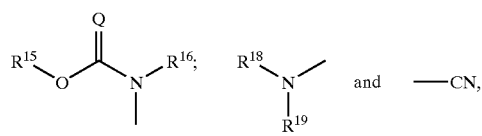

in which $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ in each case independently of one another are selected from the group consisting of hydrogen, $(C_1-C_6)$alkyl, $(C_1-C_4)$alkanoyl, t-butoxycarbonyl, benzyloxycarbonyl and benzyl, Q represents oxygen or sulphur and p is 1, 2 or 3 and with the proviso, that $R^1$ does not represent methyl, m does not represent 1, D does not represent $D_1$ and Y does not represent —$(CH_2)_3$— when Z represents a group of the formula

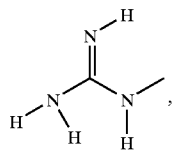

and pharmaceutically acceptable salts thereof.

2. Compounds according to claim 1 of the formula (I), in which $R^1$ represents hydrogen or $(C_1-C_6)$alkyl, X represents a group of the formula —$(CH_2)_m$—, in which m is 1 or 2, D is selected from groups of the formulae $D_1$ to $D_3$

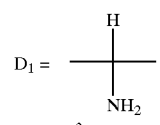

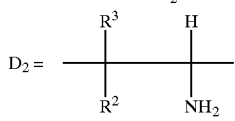

-continued

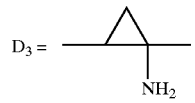

in which $R^2$ represents hydrogen or hydroxyl, $R^3$ represents hydrogen, or $R^2$ and $R^3$ together form an oxo group, Y represents a straight-chain or branched $(C_1-C_5)$ alkanediyl group which may optionally be substituted by hydroxyl or oxo, or represents a group of the formula below

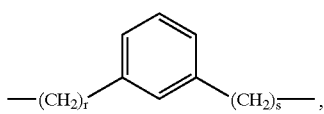

or different and are 0, 1 or 2,

Z represents a group selected from groups of the formulae

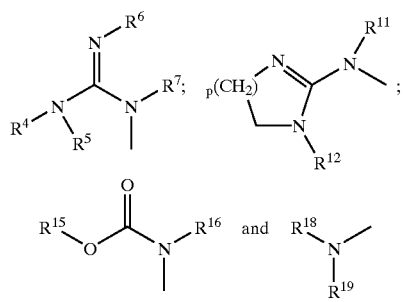

in which $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ in each case independently of one another are selected from the group consisting of hydrogen, $(C_1-C_6)$alkyl, $(C_1-C_4)$alkanoyl, carbonyl and benzyl, Q represents oxygen or sulphur and p is 1, 2 or 3 and with the proviso, that $R^1$ does not represent methyl, m does not represent 1, D does not represent $D_1$ and Y does not represent —$(CH_2)_3$— when Z represents a group of the formula

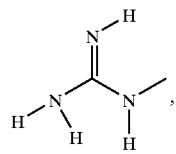

and pharmaceutically acceptable salts thereof.

3. Compounds according to claim 1 in which m is 1 or 2.

4. Compounds according to claim 1, in which Y represents a straight-chain or branched $(C_1-C_5)$alkanediyl group.

5. Compounds according to claim 1, in which Y represents a group of the formula

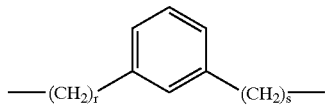

in which r and s are as defined above in claim 1.

6. Compounds according to claim 1, in which Y represents m-phenylene.

7. Compounds according to claim 1, in which r and s are 0.

8. Compounds according to claim 1, in which Z represents a group of the formula

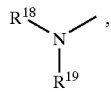

in which $R^{18}$ and $R^{19}$ are as defined in claim 1.

9. Compounds according to claim 1, in which Z represents a group of the formulae

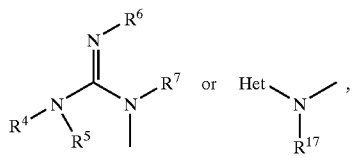

in which $R^4$, $R^5$, $R^6$, $R^7$ and $R^{17}$ are as defined in claim 1.

10. Compounds according to claim 1, in which Z represents a group of the formula

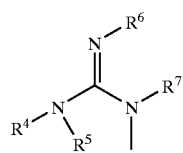

in which $R^4$, $R^5$, $R^6$ and $R^7$ are as defined in claim 1.

11. Compounds according to claim 1, in which D represents a group of the formula

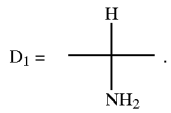

12. Compounds according to claim 1, in which D represents a group of the formula

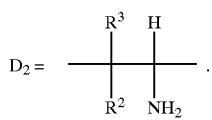

13. Compounds according to claim 1, in which D represents a group of the formula

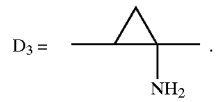

14. Compound according to claim 1 of the formula

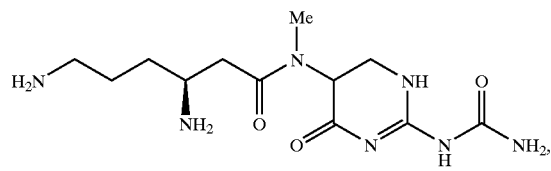

and pharmaceutically acceptable salts thereof.

15. Compound according to claim 1 of the formula

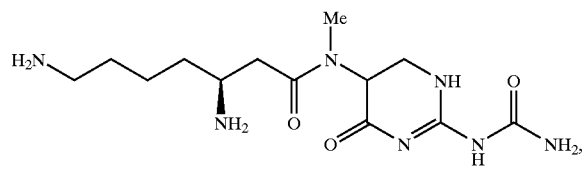

and pharmaceutically acceptable salts thereof.

16. Process for preparing compounds according to claim 1, characterized in that compounds of the formula (II)

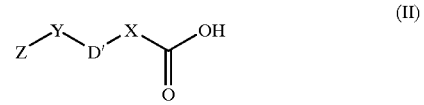

(II)

in which X, Y and Z are as defined in claim 1 and D' is selected from groups of the formulae D'1 to D'3

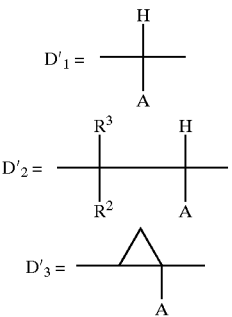

in which $R^2$ and $R^3$ are as defined in claim 1 and A is a protected amino group are reacted with compounds of the formula (III)

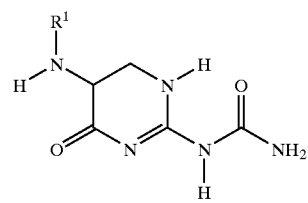

(III)

in which R¹ is as defined in claim 1, in the presence of coupling agents, and the protective group on the protected amino group A is removed.

17. Process according to claim 16, in which the coupling agent is selected from O-(7-azabenzotriazol-1-yl)-1,1,3,3-tetramethyluronium hexafluorophosphate (HATU) or bromo-tris-pyrrolidino-phosphonium hexafluorophosphate (PyBroP).

18. Pharmaceutical composition, comprising a compound according to claim 1 and a pharmaceutically acceptable carrier or excipient.

19. A method of treating an infection by gram-positive bacteria, gram-negative bacteria and corynebacteria in humans or animals, comprising administering to a human or animal an effective amount of a compound according to claim 1.

* * * * *